(12) United States Patent
Engelman et al.

(10) Patent No.: US 6,808,923 B2
(45) Date of Patent: Oct. 26, 2004

(54) EPISOMALLY REPLICATING LENTIVIRAL VECTORS

(75) Inventors: Alan Engelman, Brookline, MA (US); Wolfgang Hofmann, Bonn (DE); Joseph G. Sodroski, Medford, MA (US); Richard Lu, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/990,879

(22) Filed: Nov. 21, 2001

(65) Prior Publication Data

US 2003/0013196 A1 Jan. 16, 2003

Related U.S. Application Data

(63) Continuation of application No. PCT/US00/13715, filed on May 19, 2000.
(60) Provisional application No. 60/136,004, filed on May 26, 1999.

(51) Int. Cl.$^7$ ...................... C12N 15/867; C12N 15/63; C12N 15/64
(52) U.S. Cl. ................... 435/320.1; 435/69.1; 435/455; 435/456; 435/457; 435/325; 536/23.1; 536/23.72; 536/24.1; 536/24.5; 536/23.2; 536/23.5; 536/23.51; 536/23.52; 536/23.53
(58) Field of Search ............................ 435/320.1, 69.1, 435/455, 456, 457, 325; 536/23.1, 23.72, 24.1, 24.5, 23.2, 23.5, 23.51, 23.52, 23.53

(56) References Cited

U.S. PATENT DOCUMENTS

| 5,656,465 A | 8/1997 | Panicali et al. |
| 5,665,577 A | 9/1997 | Sodroski et al. |
| 5,681,746 A | 10/1997 | Bodner et al. |
| 5,747,307 A | 5/1998 | Lever et al. |
| 6,479,281 B1 * | 11/2002 | Gottlinger et al. ....... 435/320.1 |

FOREIGN PATENT DOCUMENTS

WO     WO 99/09139     2/1999

OTHER PUBLICATIONS

Elder et al., "Advances in Virus Research", 46:225–247 (1995).
Verma et al., "Nature", 389:239–242 (1997).
Kaplitt et al., "Nature Genetics", 8:148–154 (1994).
F. Bushman, "Science", 267:1443–1444 (1995).
Davidson et al., "Nature Genetics", 3:219–223 (1993).
Shiramizu, et al., "Cancer Research", 54:2069–2072 (1994).
Bushman et al., "J. of Virol.", 71(1):458–464 (1997).
Yang et al., "J. of Virol.", 69(4):2004–2015 (1995).
Geller et al., "Proc. Natl. Acad. Sci.", 90:7603–7607 (1993).
Geller et al., "J. of Neurochem.", 64:487–496 (1995).
Poeschla et al., "Nature Medicine", 4(3):354–357 (1998).
Cooper et al., Proc. Natl. Acad. Sci., 94:6450–6455 (1997).
Katz et al., "Virology", 217:178–190 (1996).
Haddada et al., "Curr. Top. Microbiol. Immunol.", 199:297–306 (1995).
La Salle et al., "Science", 259:988–990 (1993).

* cited by examiner

Primary Examiner—David Guzo
(74) Attorney, Agent, or Firm—Nixon Peabody LLP

(57) ABSTRACT

The invention is directed to a lentiviral vector system that can be used for episomal replication of a desired gene. The vector system contains a first vector containing a lentiviral gag gene encoding a lentiviral gag protein, a second vector containing an env gene encoding a functional envelope protein, and a lentiviral pol gene encoding a lentiviral pol protein. The pol protein is at least integrase, but that the integrase has been modified so that it is not capable of integration. This pol gene can be on the first or second vectors or on a third vector. The lentiviral gag and pol and the envelope protein are not on a single vector, and these vectors do not contain nucleotides to effectively package lentiviral RNA. The system also contains another vector having a nucleic acid sequence encoding a target molecule operably linked to a component of an episomal replicon and a lentiviral packaging sequence.

15 Claims, 8 Drawing Sheets

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: HIV-1

<400> SEQUENCE: 1 gcttttttgcc tgtactgggt ctctc                25

<210> SEQ ID NO 2
<211> LENGTH: 25
<212> TYPE: DNA
<213> ORGANISM: Artificial Sequence
<220> FEATURE:
<223> OTHER INFORMATION: HIV-1

<400> SEQUENCE: 2
caccatccaa aggtcagtgg atatc                25

<210> SEQ ID NO 3
<211> LENGTH: 21
<212> TYPE: DNA
<213> ORGANISM: Artificial Sequence
<220> FEATURE:
<223> OTHER INFORMATION: HIV-1

<400> SEQUENCE: 3
ggctaactag ggaacccact g                21

<210> SEQ ID NO 4
<211> LENGTH: 22
<212> TYPE: DNA
<213> ORGANISM: Artificial Sequence
<220> FEATURE:
<223> OTHER INFORMATION: HIV-1

<400> SEQUENCE: 4
gtcagtggat atctgatccc tg                22

EPISOMALLY REPLICATING LENTIVIRAL VECTORS

CROSS-REFERENCE TO RELATED APPLICATIONS

This application is a continuation of copending International Application PCT/US00/13715 filed on 19 May 2000 which designated the U.S. and which claims the benefit of U.S. Provisional Application No. 60/136,004, filed 26 May 1999, the content of which is relied upon and incorporated herein by reference in its entirety.

FIELD OF THE INVENTION

The present invention is directed to a viral vector that can introduce a desired nucleic acid sequence into a targeted host cell by retroviral infection where the nucleic acid sequence replicates episomally. Preferably, the viral vector is a lentiviral vector that also contains a heterologous viral origin of replication (ori) and a second gene that functions as a replication transactivator.

BACKGROUND OF THE INVENTION

In recent years considerable effort has been directed at applying gene delivery techniques. That term describes a wide variety of methods using recombinant biotechnology techniques to deliver a variety of different materials to a cell. These methods include, for example, vectors such as viral vectors, liposomes, naked DNA, adjuvant-assisted DNA, gene gun, catheters, etc. The different techniques used depend in part upon the gene being transferred and the purpose therefore. Thus, for example, there are situations where only a short-term expression of the gene is desired in contrast to situations where a longer term, even permanent expression of the gene is desired.

Vectors that have been looked at include both DNA viral vectors and RNA viral vectors. For example, DNA vectors include pox vectors such as orthopox or avipox vectors (see, e.g., U.S. Pat. No. 5,656,465), herpes virus vectors, such as herpes simplex I Virus (HSV) vector [Geller, A. I. et al., *J. Neurochem*. 64:487 (1995); Lim, F., et al., *DNA Cloning: Mammalian Systems*, D. Glover, Ed., Oxford Univ. Press, Oxford, England (1995); Geller, A. I. et al., *Proc. Natl. Acad. Sci*., U.S.A. 90:7603 (1993); Adenovirus vectors [Legal Lasalle et al., *Sci*. 259–988 (1993); Davidson et al., *Nat. Genet*. 3:219 (1993); Yang et al., *J. Virol*., 69:2004 (1995); and Adeno Associated Virus Vectors [Kaplitt, M. G., et al.]; *Nat. Genet*. 8;148 (1994)]. Retroviral vectors include moloney murine leukemia viruses (MMLV) and human immunodeficiency viruses (HIV) [See, U.S. Pat. No. 5,665,577].

For example, a retroviral vector can be used to infect a host cell and have the genetic material integrated into that host cell with high efficiency. One example of such a vector is a modified moloney murine leukemia virus (MMLV), which has had its packaging sequences deleted to prevent packaging of the entire retroviral genome. However, that retrovirus does not transduce resting cells. Additionally, since many retroviruses typically enter cells via receptors, if the specific receptors are not present on a cell or are not present in large enough numbers, the infection is either not possible or is inefficient. Concerns have also been expressed as a result of outbreaks of wild-type viruses from the recombinant MMLV producing cell lines, i.e., reversions.

Recently, attention has focused on lentiviral vectors such as those based upon the primate lentiviruses, e.g., human immunodeficiency viruses (HIV) and simian immunodeficiency virus (SIV). HIV vectors can infect quiescent cells in addition to dividing cells. Moreover, by using a pseudotyped vector (i.e., one where an envelope protein from a different species is used), problems encountered with infecting a wide range of cell types can be overcome by selecting a particular envelope protein based upon the cell you want to infect. Moreover, in view of the complex gene splicing patterns seen in a lentiviruses such as HIV, multivalent vectors (i.e., those expressing multiple genes) having a lentiviral core, such as an HIV core, are expected to be more efficient. These vectors like MMLV also result in having the genetic material integrated into the host cell with high efficiency.

Variations in the lentiviral vectors can be made where multiple modifications are made, such as deleting nef, rev, vif and vpr genes. One can also have the 3' and 5' U3 deleted LTRs.

While those vectors provide many advantages, one of their prime advantages—the ability to stably integrate into a host cell's chromosomes—can also be a major safety concern. This ability to integrate into a chromosome can cause insertional mutagenesis [Shiramiza, B., et al., *Cancer Res.*, 54:2069–2072 (1994); Verma, I. M. and Somia, N., *Nature*, 389:239–242 (1997)]. One method of dealing with this problem has been to fuse a specific DNA binding domain to the integrase (IN) polypeptide to direct integration into specific DNA sequences [Bushman, F., *Science*, 267:1443–1444 (1995); Bushman, F. and Miller, M. D., *J. Virol.*, 71:458–464 (1997); Katz, R. A., et al., *Virology*, 217:178–190 (1996)]. However, additional improvements are still useful.

Further, there are many instances where one does not want to have a gene stably integrated, but only expressed for a limited time period. For example, such as approach is useful with "suicide therapy" where the gene product is designed to negatively impact the integrity of the host cell. It is also useful with angiogenesis proteins. These proteins can promote wound healing, growth of blood vessels, etc. Thus, they can be useful in dealing with individuals having circulatory problems, heart problems etc. However, these proteins can also cause the growth of blood vessel regulated tumors. Accordingly, while some expression of the protein can be beneficial, its unlimited expression can ultimately cause more harm than benefit.

One type of expression where a gene is not integrated into a chromosome is episomal replication. Adenovirus, which replicates episomally, is the most widely used nonintegrating viral vector. It produces very high titers and has a broad target range. However, that broad target range is a disadvantage in using "suicide therapy". It would be desirable to have a method of gene therapy where one can target specific cells. In addition, adenoviruses, have immunogenicity problems [Haddada, et al., *Curr. Top. Microbiol. Immunol.*, 199:297–306 (1995); Verma and Somia, *Nature*, 389, supra.]. Thus, instances where repeated use of the vector is necessary are problematic. SV40-based vectors also replicate episomally, and have been looked at for use in suicide therapy [Cooper, M. J., et al., *Proc. Natl. Acad. Sci. USA*, 94:6450–6455 (1997)]. However, these vectors are currently introduced into cells by transfection, typically ex vivo. It would be desirable to have an alternative episomal replicating vector, that can readily be introduced into a cell.

SUMMARY OF THE INVENTION

We have now discovered a viral vector system that takes advantage of retroviral infection to bring a desired nucleic acid sequence to a targeted host cell without resulting in stable integration.

In one preferred embodiment the plurality of vectors used, include lentiviral vectors. These lentiviral vectors preferably contain a selectable marker.

The lentivirus vectors include, for example, primate lentiviruses such as human immunodeficiency virus (HIV) (e.g. HIV-1 and HIV-2) and simian immunodeficiency virus (SIV); feline immunodeficiency virus (FIV); or visna virus. The primate lentiviruses show a remarkable ability to utilize a range of heterologous envelopes resulting in pseudotyped virions.

The lentiviral virion (particle) is expressed by a vector system encoding the necessary viral proteins to produce a virion (viral particle). Preferably, there is at least one vector containing a nucleic acid sequence encoding the lentiviral pol proteins necessary for reverse transcription, operably linked to a promoter. Although the vector encoding pol sequences should not encode an IN capable of integration, it preferably does encode an IN.

For example, this can be accomplished by the substitution of sites that bind to DNA, negating the peptides ability to bind to DNA and integrate. For instance, substituting Gln for the third IN wild type active site, such as in HIV-1 (E152Q). This can be done by PCR introducing the Q into N/N yielding N/N/Q. Other changes can also be carried out. For example, if a triple leucine mutant is made it will require 9 nucleotide changes to revert all three amino acids to wild type (WT) IN. Particularly preferred are mutations to the IN-DNA binding site. These are frequently known, or can readily be determined by site-directed mutageneis. In HIV-1 such active sites include 152, 64, 116, 62, 148 and 155 [Engleman, A., et al., $J.$ $Virol.$, 71:3507–3514 (1997); Gerton, J. L., et al., $J.$ $Virol.$, 72:5046–5055 (1998)]. Preferably, one makes the most changes in these sites without substantially reducing viral replication. This can readily be determined by using known in vitro assays.

There is also a vector containing a nucleic acid sequence encoding the lentiviral gag proteins necessary for forming a viral capsid operably linked to a promoter. Preferably, this gag nucleic acid sequence is on a separate vector than at least some of the pol nucleic acid sequence, still more preferably it is on a separate vector from all the pol nucleic acid sequences that encode pol proteins.

In one embodiment, the gag sequence does not express a functional MA protein, i.e. the vector can still transduce cells in the absence of the entire MA or a portion thereof, if a myristylation anchor is provided. This can be accomplished by inactivating the "gene" encoding the MA by additions, substitutions or deletions of the MA coding region. Preferably, this is done by deletion. Preferably, at least 25% of the MA coding region is deleted, more preferably, at least 50% is deleted, still more preferably, at least 60%, even more preferably at least 75%, still more preferably, at least 90%, yet more preferably at least 95% and most preferably the entire coding region is deleted. However, in that embodiment, a myristylation anchor (sequence) is still required. Preferably, the myristylation sequence is a heterologous (i.e., non-lentiviral) sequence.

In another embodiment the lentiviral vector is another form of self-inactivating (SIN) vector as a result of a deletion in the 3' long terminal repeat region (LTR). Preferably, the vector contains a deletion within the viral promoter. The LTR of lentiviruses such as the HIV LTR contains a viral promoter. Although this promoter is relatively inefficient, when transactivated by e.g. tat, the promoter is relatively efficient. However, the presence of the viral promoter can interfere with heterologous promoters operably linked to a transgene. To minimize such interference and better regulate the expression of transgenes, the lentiviral promoter is preferably deleted.

Preferably, the vector contains a deletion within the viral promoter. The viral promoter is in the U3 region of the 3' LTR. A preferred deletion is one that is 120 base pairs between Sca I and Pvu I sites, e.g. corresponding to from nucleotides 9398–9518 of HIV, encompassing the essential core elements of the HIV-1 LTR promoter (TATA box, SP 1 and NK-Kb binding sites). After reverse transcription, the deletion is transferred to the 5' LTR, yielding a vector/provirus that is incapable of synthesizing vector transcripts from the 5' LTR in the next round of replication. Thus, the vector of the present invention contains no mechanism by which the virus can replicate as it cannot express the viral proteins.

In another embodiment the vector is a tat deleted vector. This can be accomplished by inactivating at least the first exon of tat by known techniques such as deleting it. Alternatively, one can extend the U3 LTR deletion into the R region to remove the TAR element.

Variations can be made where the lentiviral vector has multiple modifications as compared to a wildtype lentivirus. For example, with HIV being nef$^-$, rev$^-$, vif$^-$ and vpr$^-$. In addition one can have MA$^-$ gag, 3' and 5' U3 deleted LTR and variations thereof as well as the IN-inactivation.

The above-mentioned vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301–319).

The gag and pol vector(s) forming the particle preferably do not contain a nucleic acid sequence from the lentiviral genome that expresses an envelope protein. Preferably, a separate vector contains a nucleic acid sequence encoding an envelope protein operably linked to a promoter. This env vector also does not contain a lentiviral packaging sequence. In one embodiment the env nucleic acid sequence encodes a lentiviral envelope protein.

In another embodiment the envelope protein is not from the same lentivirus as the gag and pol, but from a different virus. The resultant particle is referred to as a pseudotyped particle. By appropriate selection of envelopes one can target and "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus). Other envelope proteins that can preferably be used include those from Moloney Leukemia Virus such as MLV-A, MLV-E and GALV. These envelopes are preferably when the host cell is a primary cell.

The preferred lentivirus is a primate lentivirus [U.S. Pat. No. 5,665,577] or a feline immunodeficiency virus (FIV) [Poeschla, E. M., et al., $Nat.$ $Medicine$ 4:354–357 (1998)] The pol/gag nucleic acid segment(s) and the env nucleic acid segment will when expressed produce an empty lentiviral particle. By making the above-described modifications such as inactivating IN, deleting, the MA coding region, or the U3 region of the LTR, the possibility of a reversion to a wild type virus has been reduced.

A desired family of heterologous nucleic acid segment (sometimes referred to as the target molecule) can be inserted into the empty lentiviral particles by use of a plurality of vectors each containing a nucleic acid segment of interest and a lentiviral packaging sequence necessary to package lentiviral RNA into the lentiviral particles (the packaging vector). Preferably, the packaging vector contains a 5' and 3' lentiviral LTR with the desired nucleic acid segment inserted between them. The nucleic acid segment can be antisense molecules or more preferably, encodes a protein such as an antibody. The packaging vector preferably contains a selectable marker. These are well known in the art and include genes that change the sensitivity of a cell to a stimuli such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

The packaging vector also contains at least one component of the episomal replicon. Preferably, one uses a DNA viral replicon. DNA viruses that can be used include SV40 Epstein-Barr virus (EBV) and BK virus [Cooper, M. J., et al., *Proc. Natl. Acad. Sci. USA*, 94, supra; Eckhart, W., *Virology* 38:120–125 (1969); Asconzioni, F., et al., *Cancer Lett.*, 118:135–142 and Fried, M., *Proc. Natl. Acad. Sci. USA*, 53:486–491 (1965)]. The replicon comprises a viral DNA origin of replication (ori) and a protein that acts as a replication transactivator. Typically, that protein is an early gene product from the same virus. However, other constructs can be used. [See for example, Piechaczek, C., et al., *Nucleic Acids Research*, 27:426–428 (1999)]. Because the viral proteins such as large T-antigen for SV40, EBNA-1 for EBV, and large T-antigen for BK virus are transforming (i.e. tumorigenic), the use of modified constructs is preferred. For example, deleting domains that bind human tumor suppressor gene products such as p53, retinoblastoma and p107. One such construct is the SV40 mutant 107/402-T which encodes a lysine instead of glutamic acid at codon 107 and glutamic acid instead of aspartic acid at codon 402. Other amino acids can also be substituted. Binding activity can readily be determined in an in vitro assay by known means. Another construct that can be used instead of SV40 T-antigen is the S/MAR (scaffold/matrix attached region) fragment from a gene such as the human interferon β-gene.

These regions are typically about 70%, A/T-rich sequences and are often associated with chromosomal origins of bidirectional replication [Piechaczek, C., *Nucleic Acids Research*, supra; Bode, J., *Science*, 255:195–197 (992); Luderus, M. E., et al., *Mol. Cell Biol.*, 14:6297–6305 (1994)].

Both the ORI and the transactivating protein can be on the packaging vector. Alternatively, the transactivating protein can be on a separate vector.

In one embodiment, the vector containing the gene encoding the transactivating protein is not added to the host cell at the same time, but only at a later time—in a manner analogous to use of an inducible promoter.

The advantage of such a method is to minimize the phenomenon of "gene silencing" that is sometimes encountered. Other methods to avoid this problem can also be used.

For example, when an inducible promoter is used with the target molecule, minimal selection pressure is exerted on the transformed cells for those cells where the target molecule is "silenced". If one also uses a marker gene, the identification of cells displaying the marker also identifies cells that can express the target molecule. If an inducible promoter is not used, it is sometimes preferable to use a "forced-expression" system where the target molecule is linked to the selectable marker by use of an internal ribosome entry site (IRES) (see Marasco et al., PCT/US96/16531).

IRES sequences are known in the art and include those from encephalomycarditis virus (EMCV) [Ghattas, I. R. et al., *Mol. Cell. Biol.*, 11:5848–5849 (1991); BiP protein [Macejak and Sarnow, *Nature*, 353:91 (1991)]; the Antennapedia gene of drosophilia (exons d and e) [Oh et al., *Genes & Development*, 6:1643–1653 (1992)]; those in polio virus [Pelletier and Sonenberg, *Nature*, 334:320325 (1988); see also Mountford and Smith, TIG, 11:179–184 (1985)].

Inducible promoters include those using the lac repressor from *E. coli* as a transcription modulator to regulate transcription from lac operator-bearing mammalian cell promoters [Brown, M. et al., *Cell*, 49:603–612 (1987)], those using the tetracycline repressor (tetR) [Gossen, M., and Bujard, H., *Proc. Natl. Acad. Sci USA* 89:5547–5551 (1992); Yao, F. et al., *Human Gene Therapy*, 9:1939–1950 (1998); Shockelt, P., et al., *Proc. Natl. Acad. Sci. USA*, 92:6522–6526 (1995)]. See Miller, N. and Whelan, J., *Human Gene Therapy*, 8:803–815 (1997). Other systems include FK506 dimer, VP16 or p65 using astradiol, RU486, diphenol murislerone or rapamycin [see Miller and Whelan, supra at FIG. 2]. Inducible systems are available from Invitrogen, Clontech and Ariad. Systems using a repessor with the operon are preferred. Regulation of transgene expression in target cells represents a critical aspect of gene therapy. For example, the lac repressor from *Escherichia coli* can function as a transcriptional modulator to regulate transcription from lac operator-bearing mammalian cell promoters [M. Brown et al., *Cell*, 49:603–612 (1987)]; Gossen and Bujard (1992); [M. Gossen et al., *Natl. Acad. Sci. USA*, 89:5547–5551 (1992)] combined the tetracycline repressor (tetr) with the transcription activator (VP16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. Recently Yao and colleagues [F. Yao et al., *Human Gene Therapy*, supra] demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells [M. Gossen et al., *Natl. Acad. Sci. USA*, 89:5547–5551 (1992); P. Shockett et al., *Proc. Natl. Acad. Sci. USA*, 92:6522–6526 (1995)], to achieve its regulatable effects. Preferably, the repressor is linked to the target molecule by an IRES sequence. Preferably, the inducible system is a tetR system. More preferably the system has the tetracycline operation downstream of a promoter's TATA element such as with the CMVIE promoter.

BRIEF DESCRIPTION OF THE DRAWINGS

FIG. 1A shows Jurkat cells infected with WT (~), N/N (O), E/E (−), 1–212 (x), U3U5 (□) or mock infected (+). FIG. 1B shows C8166 cells infected as described in FIG. 1A. FIG. 1C shows MT-4 cells infected WT (~), N/N (O), E/E (−), 1–212 (x) or mock infected (+). FIG. 1D shows CEMx174 cells were infected overnight with WT (~), N/N (0) or mock infected (+). FIG. 1E shows MT-4 cells infected with WT (~), N/N (O), NNQ (–), NNQ/LTR (□) or mock infected (+). Culture supernatants were tested for RT activity at the indicated times.

Figure 2A:
Figure 2B:
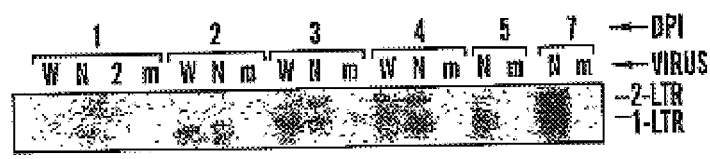
Figure 2C:
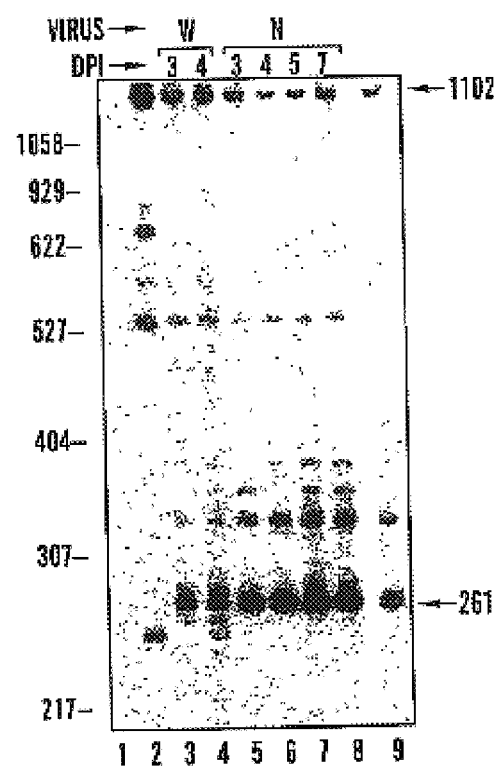

FIGS. 2A–2C show HIV-1 replication in MT-4 cells in the absence of IN-mediated recombination. Cells ($10^8$) were infected with $10^9$ RT-cpm for 2 hr at 37° C. FIG. 2A shows Cytoplasmic extracts of WT (W), N/N (N), 1–212 (2) and mock (m)-infected cells lysed at the indicated times. Three different DNAs, most likely linear, 1-LTR and 2-LTR circles, were detected. Circular DNA was recovered due to loss of nuclear integrity during virus replication. FIG. 2B shows unintegrated nuclear DNA. The migration positions of 1-LTR and 2-LTR circles are indicated; linear DNA was absent due to alkaline lysis. Levels of unintegrated DNA were quantified using both FIGS. 2A and 2B. FIG. 2C shows inverse PCR. Lane 1, genomic DNA from mock-infected cells; lane 2, 1 ng of pNL4–3 mixed with 10 μg of mock-infected genomic DNA prior to Hind III digestion; lanes 3–8, as indicated; lane 9, 10 μg mock-infected DNA mixed with Hirt supernatant from approximately $5 \times 10^4$ N/N-infected cells. Inverse PCR detects left- and right-end Hind III fragments following intramolecular ligation (Lewis et al., 1992). Both integrated and unintegrated DNAs yield a 1,102 bp right-end product; 2-LTR circles yield an additional 261 bp circle junction product. Integrated proviruses yield a population of left-end products wherein each product reflects the distance between the viral Hind III site at position 531 and the adjacent upstream cellular site (lanes 3 and 4). Some of the infected cell products resulted from nonspecific amplification (~530 bp in lane 2) or amplification of 2-LTR circles in the genomic DNA fractions (lane 9). The migration positions of molecular mass standards are indicated on the left.

Figure 3:
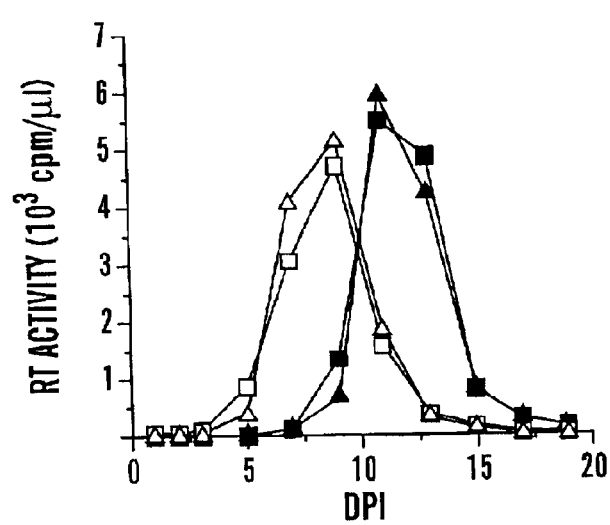

FIG. 3 shows growth kinetics of WT, N/N and N/N.oriT in 1D cells. Cells infected with $10^7$ RT-cpm of WT (~), N/N (×) or N/N.oriT (–); cells infected with $10^5$ RT-cpm of WT (□) or N/N.oriT (◻). Cell supernatants were assayed for RT activity at the indicated times.

Figure 4A:
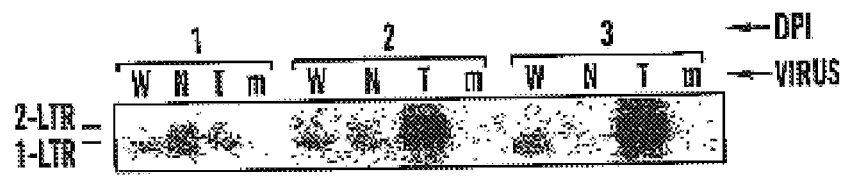
Figure 4B:
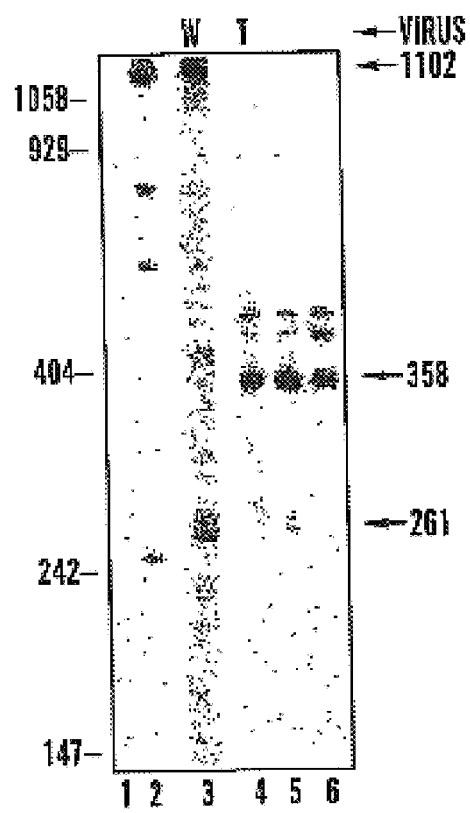

FIGS. 4A and 4B show N/N.oriT replication in 1D cells in the absence of integration. Cells ($1.6 \times 10^8$) were infected with $8.0 \times 10^8$ RT-cpm for 4 hr at 37° C. FIG. 4A shows unintegrated nuclear DNA from WT (W), N/N (N), N/N.oriT (T) and mock (m)-infected cells lysed at the indicated times. The first four lanes were exposed to film overnight; other lanes were exposed to film for 3 hr. FIG. 4B shows inverse PCR. Lane 1, genomic DNA from mock-infected cells; lane 2, 10 μg mock-infected DNA plus 1 ng pNL4–3; lanes 3 and 4, genomic DNA isolated 3 Dpi with the indicated viruses; lane 5, mock-infected DNA plus Hirt supernatant from approximately $10^4$ N/N.oriT-infected cells; lane 6, mock-infected DNA plus pN/N.oriT (oriT contains a Hind III site, thus, the WT 1,102 bp right-end product was 358 bp in N/N.oriT). The gel in lane 3 was exposed to film overnight; the gel in lanes 1, 2 and 4–6 was exposed to film for 5 hr. The longer exposure did not reveal evidence of IN-mediated recombination in N/N.oriT-infected cells. Other labeling is the same as in FIG. 2.

Figure 5A:
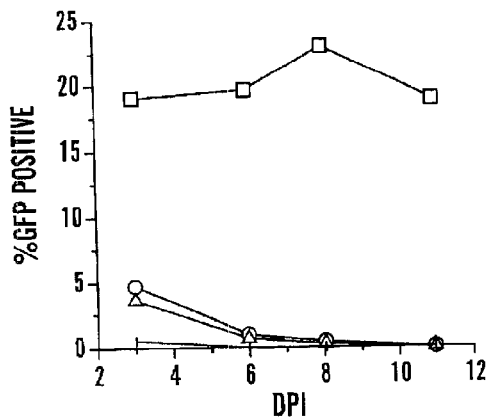
Figure 5B:
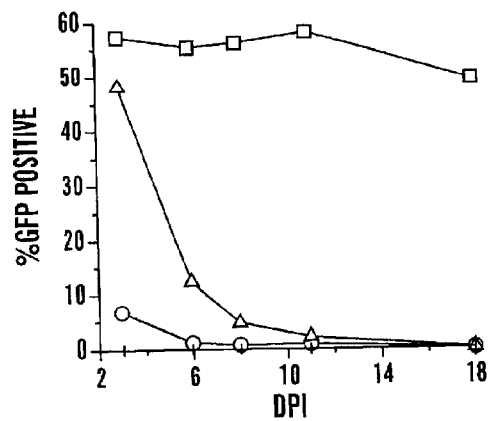
Figure 5C:
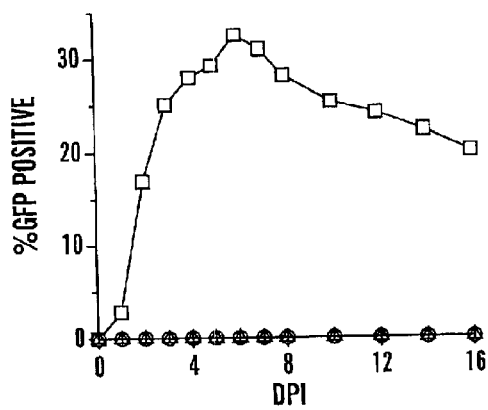
Figure 5D:
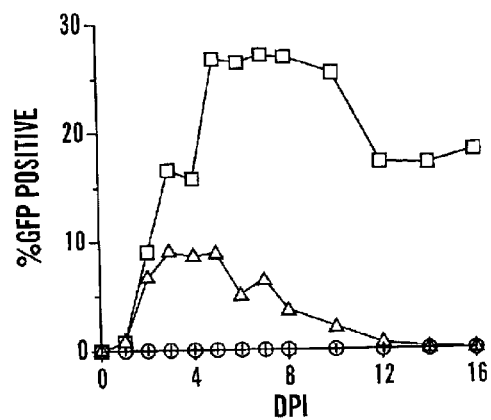

FIGS. 5A–5D show transient gene expression from episomal HIV-1. FIG. 5A shows CV-1 cells infected with WT.GFP (~), D116A.GFP (O), D116A.GFP.oriT (–) or mock infected (+). Cells were analyzed for GFP expression at the indicated times. FIG. 5B shows COS-1 cells treated as described in FIG. 5A. FIG. 5C shows Jurkat cells treated as described in FIG. 5A. FIG. 5D Jurkat TAg cells treated as described in FIG. 5A.

Figure 6A:
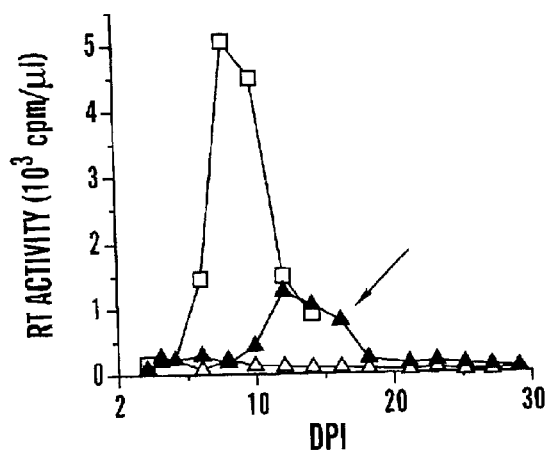
Figure 6B:
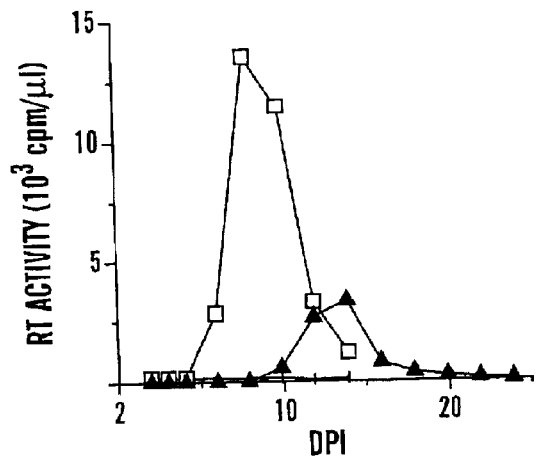
Figure 6C:
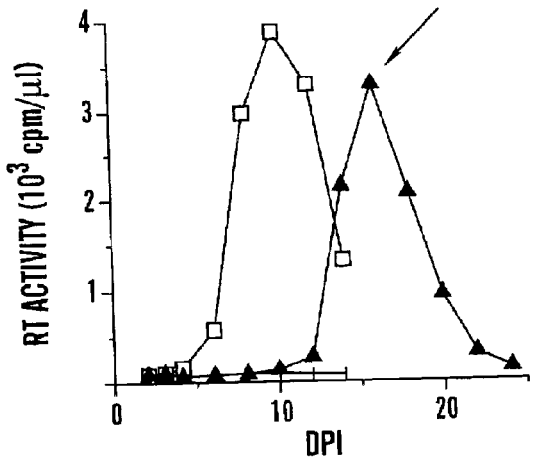

FIGS. 6A–6C show N/N.TAg-oriT replication in Jurkat cells. FIG. 6A shows cells infected with $10^6$ RT-cpm of HeLa-derived WT (~), N/N.TAg-oriT (□), N/N.U19-oriT (–), or mock infected (+). FIG. 6B shows cells infected with $10^6$ RT-cpm of the indicated viruses derived from panel a. FIG. 6C shows cells infected with $10^5$ RT-cpm of panel a derived viruses. Culture supernatants were tested for RT activity at the indicated times. Arrows in FIGS. 6A and 6C indicate cultures lysed by Hirt extraction.

Figure 7A:
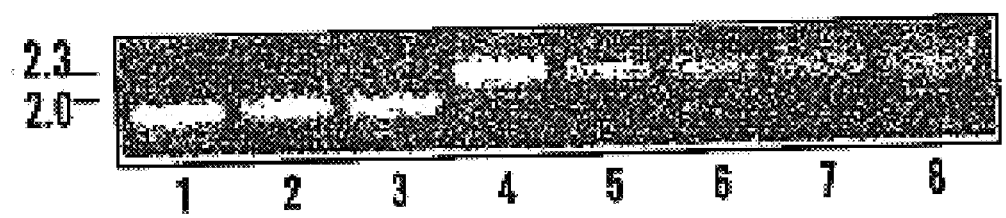
Figure 7B:
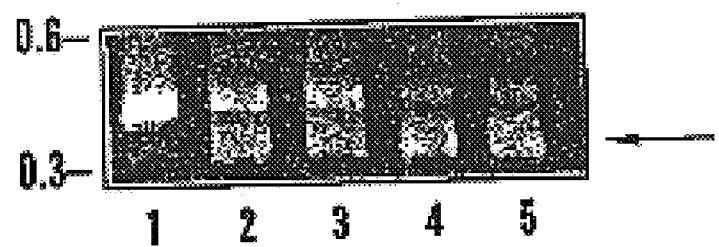

FIGS. 7A and 7B show PCR analysis of replicated N/N.TAg-oriT. FIG. 7A shows Agarose gel. Lane 1, IN-containing pol fragment amplified for 20 cycles from pN/N.TAg-oriT with Pfu polymerase; lane 2, Hirt supernatant from ~$5 \times 10^4$ second round infected cells (FIG. 6C); lane 3, same as lane 2 except lysate was treated with Dpn I before PCR. Lane 4, TAg amplified from plasmid; lanes 5 and 6, minus and plus Dpn I, respectively, of first round Hirt supernatant (FIG. 6A); lanes 7 and 8, – and +Dpn I, respectively, of second round lysate (FIG. 6C). FIG. 7B shows Acrylamide gel. Lane 1, oriT amplified from plasmid using AmpliTaq polymerase; lanes 2 and 3, – and +Dpn I from first round lysate; lanes 4 and 5, – and +Dpn I from second round lysate. The arrow marks the smaller oriT fragment that accumulated during passage. DNA was detected by staining with ethidium bromide. Sizes in kb are marked to the left of each gel.

Figure 8:
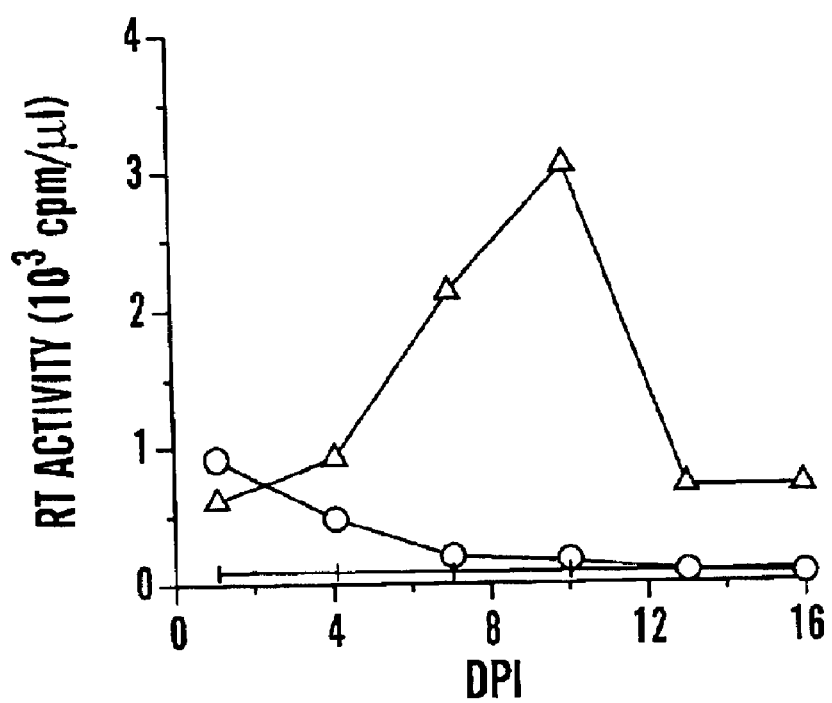

FIG. 8 shows TAg-oriT requirement for IN mutant replication in MDM. MDM infected with N/N(AD8) (O), N/N.TAg-oriT(AD8) (–), or mock infected (+). Culture supernatants were tested for RT activity at the indicated times. Whereas N/N.TAg-oriT(AD8) yielded ~3,050 RT-cpm/μl, WT(AD8) yielded ~24,700 RT-cpm/μl 10 Dpi.

DETAILED DESCRIPTION OF THE INVENTION

We have now discovered a viral vector system that takes advantage of retroviral infection to bring a desired nucleic acid sequence to a targeted host cell without resulting in stable integration.

Retroviral virions carry two enzymes, reverse transcriptase (RT) and integrase (IN), which function early in the viral life cycle. Soon after infection, RT converts genomic RNA into linear double-stranded cDNA. This DNA, which contains a copy of the viral long terminal repeat (LTR) at each end, is the substrate for IN-medialted DNA recombination. IN initially processes the 3' ends of the cDNA, and subsequently inserts the processed ends into an acceptor site in a host cell chromosome. The cis-acting regions of the viral ends important for integration define the DNA attachment (att) site, which is comprised of U3 and U5 sequences in the upstream and downstream LTRs, respectively. See Brown (1997).

In addition to the linear DNA product of reverse transcription, various types of circular viral DNA form in retroviral-infected cells. Whereas some of these result from IN-mediated autointegration of the viral cDNA into itself, others result from host-mediated enzyme activities. There are two types of host-mediated circles. One, which contains a single copy of the LTR, most likely forms by homologous recombination between the LTRs, although aberrant reverse transcription has been suggested (for review, see Telesnitsky and Goff, 1997). The other host-mediated circle contains two tandem LTRs, and probably forms by ligating the two ends of linear cDNA together. Host-mediated DNA circles are generally considered to be dead end products of reverse transcription (Brown, 1997). By using a viral system wherein IN has been modified so that it no longer inserts the processed ends into an acceptor site in a host cell's chromosome, integration will no longer occur.

In one preferred embodiment the plurality of vectors used, include lentiviral vectors. These lentiviral vectors preferably contain a selectable marker.

The lentivirus vectors include, for example, primate lentiviruses such as human immunodeficiency virus (HIV) (e.g. HIV-1 and HIV-2) and simian immunodeficiency virus (SIV); feline immunodeficiency virus (FIV); or visna virus. The primate lentiviruses show a remarkable ability to utilize a range of heterologous envelopes resulting in pseudotyped virions.

The lentiviral virion (particle) is expressed by a vector system encoding the necessary viral proteins to produce a virion (viral particle). Preferably, there is at least one vector containing a nucleic acid sequence encoding the lentiviral pol proteins necessary for reverse transcription, operably linked to a promoter. Although the vector encoding pol sequences should not encode an IN capable of integration, it preferably does encode an IN. Whereas we disclose that lentiviruses such as UV-1 efficiently replicated in the absence of integration, the presence of the IN polypeptide, although nonfunctional under these conditions, could effect virus growth. This is due to pleiotropic effects of IN deletions, as well as some single amino acid changes, on the HIV-1 life cycle (reviewed in Engelman, 1999).

Preferred substitutions are those that inactivate integrase functions without stopping viral replication. For example, this can be accomplished by the substitution of sites that bind to DNA, negating the peptides ability to bind to DNA and integrate. For instance, substituting Gln for the third IN wild type active site, such as in HIV-1 (E 152Q). This can be done by PCR introducting the Q into N/N yielding N/N/Q. Other changes can also be carried out. For example, if a triple leucine mutant is made it will require 9 nucleotide changes to revert all three amino acids to wild type (WT) IN. Particularly preferred are mutations to the IN-DNA binding site. These are frequently known, or can readily be determined by site-directed mutageneis. In HIV-1 such active sites include 152, 64, 116, 62, 148 and 155 [Engleman, A., et al., *J. Virol.*, 71:3507–3514 (1997); Gerton, J. L., et al., *J. Virol.*, 72:5046–5055 (1998)]. Preferably, one makes the most changes in these sites without substantially reducing viral replication. This can readily be determined by using known in vitro assays.

For example, we have shown that the 1–212 class II IN deletion mutant was not only replication-defective in highly permissive MT-4 cells (FIG. 1b), but 1–212 carrying oriT did not detectably replicate in infected TAg-expressing 1D Jurkat cells (data not shown). These results highlight the advantage of creating a relatively unperturbed IN protein domain during HIV-1 particle assembly (Bukovsky and G öttlinger, 1996) for subsequent virus infectivity. However, by determining the domains necessary for viral replication for instance by creating a range of deletion mutants, one can readily determine which deletions one should not make.

There is also a vector containing a nucleic acid sequence encoding the lentiviral gag proteins necessary for forming a viral capsid operably linked to a promoter. Preferably, this gag nucleic acid sequence is on a separate vector than at least some of the pol nucleic acid sequence, still more preferably it is on a separate vector from all the pol nucleic acid sequences that encode pol proteins.

In one embodiment, the gag sequence does not express a functional MA protein, i.e. the vector can still transduce cells in the absence of the entire MA or a portion thereof, if a myristylation anchor is provided. This can be accomplished by inactivating the "gene" encoding the MA by additions, substitutions or deletions of the MA coding region. Preferably, this is done by deletion. Preferably, at least 25% of the MA coding region is deleted, more preferably, at least 50% is deleted, still more preferably, at least 60%, even more preferably at least 75%, still more preferably, at least 90%, yet more preferably at least 95% and most preferably the entire coding region is deleted. However, in that embodiment, a myristylation anchor (sequence) is still required. Preferably, the myristylation sequence is a heterologous (i.e., non-lentiviral) sequence.

In another embodiment the lentiviral vector is another form of self-inactivating (SIN) vector as a result of a deletion in the 3' long terminal repeat region (LTR). Preferably, the vector contains a deletion within the viral promoter. The LTR of lentiviruses such as the HIV LTR contains a viral promoter. Although this promoter is relatively inefficient, when transactivated by e.g. tat, the promoter is relatively efficient. However, the presence of the viral promoter can interfere with heterologous promoters operably linked to a transgene. To minimize such interference and better regulate the expression of transgenes, the lentiviral promoter is preferably deleted.

Preferably, the vector contains a deletion within the viral promoter. The viral promoter is in the U3 region of the 3' LTR. A preferred deletion is one that is 120 base pairs between Sca I and Pvu I sites, e.g. corresponding to from nucleotides 9398–9518 of HIV, encompassing the essential core elements of the HIV-1 LTR promoter (TATA box, SP 1 and NK-Kb binding sites). After reverse transcription, the deletion is transferred to the 5' LTR, yielding a vector/ provirus that is incapable of synthesizing vector transcripts from the 5' LTR in the next round of replication. Thus, the vector of the present invention contains no mechanism by which the virus can replicate as it cannot express the viral proteins.

In another embodiment the vector is a tat deleted vector. This can be accomplished by inactivating at least the first exon of tat by known techniques such as deleting it. Alternatively, one can extend the U3 LTR deletion into the R region to remove the TAR element.

Variations can be made where the lentiviral vector has multiple modifications as compared to a wildtype lentivirus. For example, with HIV being nef⁻, rev⁻, vif⁻ and vpr⁻. In addition one can have MA⁻ gag, 3' and 5' U3 deleted LTR and variations thereof as well as the IN-inactivation.

The above-mentioned vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301–319).

The gag and pol vector(s) forming the particle preferably do not contain a nucleic acid sequence from the lentiviral genome that expresses an envelope protein. Preferably, a separate vector contains a nucleic acid sequence encoding an envelope protein operably linked to a promoter. This env vector also does not contain a lentiviral packaging sequence. In one embodiment the env nucleic acid sequence encodes a lentiviral envelope protein.

In another embodiment the envelope protein is not from the same lentivirus as the gag and pol, but from a different virus. The resultant particle is referred to as a pseudotyped particle. By appropriate selection of envelopes one can target and "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus), rhabdoviruses (vesicular stomatitis virus, rabies virus), and orthomyxoviruses (influenza virus). Other envelope proteins that can preferably be used include those from Moloney Leukemia Virus such as MLV-A, MLV-E and GALV. These envelopes are preferably when the host cell is a primary cell.

The packaging sequence can be excluded from the vector (s) by any of a variety of techniques well known to the person of ordinary skill in the art. For example, one can simply delete the entire sequence. Alternatively, one can delete a sufficient portion of a sequence to render it incapable of packaging. An alternative strategy is to insert nucleotides into such a site to render it non-functional. Most preferably, one will delete the site entirely to prevent homologous recombination.

Accordingly, the lentiviral vectors can express the desired viral proteins, but because the packaging site has been removed, the resultant RNA segment will not have packaging sequences that will cause that RNA to be packaged into the lentiviral particles, and the recombinant virus will not be able to replicate and infect other cells.

The lentiviral vectors can also contain sequences encoding desired lentiviral regulatory proteins such as Tat, Rev, etc. However, in a number of embodiments it is preferable not to contain such regulatory genes. If RRE and CAR sequences are included in the gene, the inclusion of sequence encoding RRE is necessary, unless the virus is expressed in the cytoplasm. These regulatory sequences can be on the other lentiviral vectors (e.g., gag vector, pol vector, or env vector), or on their own lentiviral vector.

The preferred lentivirus is a primate lentivirus [U.S. Pat. No. 5,665,577] or a feline immunodeficiency virus (FIV) [Poeschla, E. M., et al., Nat. Medicine 4:354–357 (1998)] The pol/gag nucleic acid segment(s) and the env nucleic acid segment will when expressed produce an empty lentiviral particle. By making the above-described modifications such as inactivating IN, deleting, the MA coding region, or the U3 region of the LTR, the possibility of a reversion to a wild type virus has been reduced.

A desired family of heterologous nucleic acid segment (sometimes referred to as the target molecule) can be inserted into the empty lentiviral particles by use of a plurality of vectors each containing a nucleic acid segment of interest and a lentiviral packaging sequence necessary to package lentiviral RNA into the lentiviral particles (the packaging vector). Preferably, the packaging vector contains a 5' and 3' lentivilral LTR with the desired nucleic acid segment inserted between them. The nucleic acid segment can be antisense molecules or more preferably, encodes a protein such as an antibody. The packaging vector preferably contains a selectable marker. These are well known in the art and include genes that change the sensitivity of a cell to a stimuli such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

The heterologous nucleotide sequence can encode a wide variety of proteins such as a therapeutic protein, i.e., one that compensates for an inherited or acquired deficiency. Another sequence is a suicide gene, i.e. one that encodes a protein that kills a cell, such as ricin. Examples of therapeutic proteins include neurotransmitter biosynthetic enzymes, e.g., tyrosine hydroxylase for the treatment of Parkinson's disease; neurotrophic factors including neurotrophins, e.g., nerve growth factor for the treatment of Alzheimer's disease, one can also use nerve growth factor receptor and the trk receptor; hypoxanthine-guanine porphoribosyl transferase (HGPRT) for the treatment of Lesch Nyhan disease; β-hexosaminadase a chain for the treatment of tay Sachs disease; insulin for the treatment of diabetes. Receptors can also be prepared, e.g. the nerve growth factor receptor, the trk receptor, etc. Because the insert can be large, it is possible to encode a series of different proteins. For example, one can encode a series of proteins that form a receptor-ligand complex.

Other proteins, include, for example, signal transduction enzymes, e.g., protein kinase c; transcription factors, e.g., c-fos, NF-Kβ; oncogenes, e.g., erbB, erbB-2/neu, ras; neurotransmitter receptors, e.g., glutamate receptor, dopamine receptor, etc.

One preferred group of proteins are antibodies. Included are dAbs, single chain antibodies, Fabs. Single chain antibodies are preferred. Libraries of antibodies are known and can be used in the present invention.

The heterologous nucleotide sequence can also encode antisense molecules (DNA or RNA). These molecules can be used to regulate gene expression associated with a particular disease. The antisense molecules are obtained from a nucleotide sequence by reversing the orientation of the coding region with regard to the promoter. Thus, the antisense RNA is complimentary to the corresponding mRNA. For review of antisense science see Green, et al., Ann. Rev. Biochem. 55:569–597 (1986), which is herein incorporated by reference. The antisense sequence can contain modified sugar phosphate backbones to increase stability and make them less sensitive to RNA sensitivity. Examples of the modifications are described by Rossi, et al., Pharmacol. Ther. 50(2):245–354 (1991). Another class of molecule includes ribozymes. Ribozymes and antisense molecules that engage in, as well as those that do not show transplicing can be used.

The heterologous nucleotide sequence is preferably operably linked to a promoter sequence capable of directing transcription of the sequence in a desired target cell. Lentiviruses such as the primate lentiviruses contain the Tat regulatory protein. This protein will transactivate a protein operably linked to a TAR element. The TAR element is present in the 5' LTR of the primate lentivirus. Thus, the expression of heterologous protein can be enhanced by transactivation. The LTR also contains a promoter. However, that promoter in the absence of transactivation is relatively ineffective. Thus, the use of other promoters and enhancers is typically preferred. The promoter can be a promoter such as the SV40, CMV, HSV-1 IE, IE 4/5 or RSV (Rous sarcoma virus) promoters. Others include Srα-promoter (a very strong hybrid promoter composed of the SV40 early promoter fused to the R/U5 sequences from the HTLV-I LTR), tetracycline-regulatable promoters, tissue-specific promoters (e.g., alpha-fetoprotein promoter; and rhodopsin promoter for photoreceptor-targeted expression). Other promoters capable of directing transcription of the heterologous sequence in a specific target cell can also be used. For example, if the target cell is a neuronal cell, a promoter such as the neuron specific enolase promoter (Forss-Petter, et al., (1986)) can be used. The rat tyrosine hydroxylase (TH) promoter can support cell type specific expression in the midbrain (Song, et al., (1995). Furthermore, the use of inducible promoters or other inducible regulatory sequences, which are well known in the art, in some embodiments are preferred. For example, the tetR-tetO system. As discussed the promoter in the LTR can interfere with the other promoter. Thus, in certain embodiments it is preferable to inactivate the viral LTR promoter.

The packaging vector also contains at least one component of the episomal replicon. Preferably, one uses a DNA viral replicon. DNA viruses that can be used include SV40 Epstein-Barr virus (EBV) and BK virus [Cooper, M. J., et al., *Proc. Natl. Acad. Sci. USA*, 94, supra; Eckhart, W., *Virology* 38:120–125 (1969); Asconzioni, F., et al., *Cancer Lett.*, 118:135–142 and Fried, M., *Proc. Natl. Acad. Sci. USA*, 53:486–491 (1965)]. The replicon comprises a viral DNA origin of replication (ori) and a protein that acts as a replication transactivator. Typically, that protein is an early gene product from the same virus. However, other constructs can be used. [See for example, Piechaczek, C., et al., *Nucleic Acids Research*, 27:426–428 (1999)]. Because the viral proteins such as large T-antigen for SV40, EBNA-1 for EBV, and large T-antigen for BK virus are transforming (i.e. tumorigenic), the use of modified constructs is preferred. For example, deleting domains that bind human tumor suppressor gene products such as p53, retinoblastoma and p107. One such construct is the SV40 mutant 107/402-T which encodes a lysine instead of glutamic acid at codon 107 and glutamic acid instead of aspartic acid at codon 402. Other amino acids can also be substituted. Binding activity can readily be determined in an in vitro assay by known means. Another construct that can be used instead of SV40 T-antigen is the S/MAR (scaffold/matrix attached region) fragment from a gene such as the human interferon β-gene.

These regions are typically about 70%, A/T-rich sequences and are often associated with chromosomal origins of bidirectional replication [Piechaczek, C., *Nucleic Acids Research*, supra; Bode, J., *Science*, 255:195–197 (1992); Luderus, M. E., et al., *Mol. Cell Biol.*, 14:6297–6305 (1994)].

Both the ORI and the transactivating protein can be on the packaging vector. Alternatively, the transactivating protein can be on a separate vector.

In one embodiment, the vector containing the gene encoding the transactivating protein is not added to the host cell at the same time, but only at a later time—in a manner analogous to use of an inducible promoter.

The advantage of such a method is to minimize the phenomenon of "gene silencing" that is sometimes encountered. Other methods to avoid this problem can also be used.

For example, when an inducible promoter is used with the target molecule, minimal selection pressure is exerted on the transformed cells for those cells where the target molecule is "silenced". If one also uses a marker gene, the identification of cells displaying the marker also identifies cells that can express the target molecule. If an inducible promoter is not used, it is sometimes preferable to use a "forced-expression" system where the target molecule is linked to the selectable marker by use of an internal ribosome entry site (IRES) (see Marasco et al., PCT/US96/16531).

IRES sequences are known in the art and include those from encephalomycarditis virus (EMCV) [Ghattas, I. R. et al., *Mol. Cell. Biol.*, 11:5848–5849 (1991); BiP protein [Macejak and Sarnow, *Nature*, 353:91 (1991)]; the Antennapedia gene of drosophilia (exons d and e) [Oh et al., *Genes & Development*, 6:1643–1653 (1992)]; those in polio virus [Pelletier and Sonenberg, *Nature*, 334:320325 (1988); see also Mountford and Smith, TIG, 11:179–184 (1985)].

Inducible promoters include those using the lac repressor from *E. coli* as a transcription modulator to regulate transcription from lac operator-bearing mammalian cell promoters [Brown, M. et al., *Cell*, 49:603–612 (1987)], those using the tetracycline repressor (tetR) [Gossen, M., and Bujard, H., *Proc. Natl. Acad. Sci. USA* 89:5547–5551 (1992); Yao, F. et al., *Human Gene Therapy*, 9:1939–1950 (1998); Shockelt, P., et al., *Proc. Natl. Acad. Sci. USA*, 92:6522–6526 (1995)]. See Miller, N. and Whelan, J., *Human Gene Therapy*, 8:803–815 (1997). Other systems include FK506 dimer, VP16 or p65 using astradiol, RU486, diphenol murislerone or rapamycin [see Miller and Whelan, supra at FIG. 2]. Inducible systems are available from Invitrogen, Clontech and Ariad. Systems using a repressor with the operon are preferred. Regulation of transgene expression in target cells represents a critical aspect of gene therapy. For example, the lac repressor from *Escherichia coli* can function as a transcriptional modulator to regulate transcription from lac operator-bearing mammalian cell promoters [M. Brown et al., *Cell*, 49:603–612 (1987)]; Gossen and Bujard (1992); [M. Gossen et al., *Natl. Acad. Sci. USA*, 89:5547–5551 (1992)] combined the tetracycline repressor (tetR) with the transcription activator (VP16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. Recently Yao and colleagues [F. Yao et al., *Human Gene Therapy*, supra] demonstrated that the tetracycline repressor (tetR) alone, rather than the tetR-mammalian cell transcription factor fusion derivatives can function as potent transmodulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells [M. Gossen et al., *Natl. Acad. Sci. USA*, 89:5547–5551 (1992); P. Shockett et al., *Proc. Natl. Acad. Sci;. USA*, 92:6522–6526 (1995)], to achieve its regulatable effects. Preferably, the repressor is linked to the target molecule by an IRES sequence. Preferably, the inducible system is a tetR system. More preferably the system has the tetracycline operation downstream of a promoter's TATA element such as with the CMVIE promoter.

In order to minimize the possibility of a recombination event between the packaging vector and the lentiviral vector generating a wild type lentivirus, it is desirable that the packaging vector has a minimal degree of homology with the nucleotide segments encoding the particle vector. Preferably, one would use different promoters in these different vectors. These goals can be accomplished by a variety of means known in the art based upon the present disclosure.

Alternatively or in combination with the above approach of reducing homology, one can alter the sequence of a gene from the lentivirus segment so that it does not encode a functional protein. As used herein "functional" means a protein having wild-type activity.

Depending upon the particular purpose for the particles one can use known techniques to alter the lentivirus segment to inactivate genes that encode proteins present in the particle which cause certain effects. For example, inactivating those proteins that enhance replication, e.g., rev and/or tat. Vpu affects infectivity. Nef also affects the virus. It has been reported that nef appears to be required for efficient replication in vivo.

Cells can be transfected by the vectors to prepare the viral particle. One can prepare the vectors in vitro, one would then harvest the particles, purify them and inject them by means well known in the art. More preferably one would purify the particles, and then use those to infect the desired cells.

These vectors can be used to express large amounts of viral particles. This requires transfecting a cell with the particle vector system described herein, the packaging vector, and culturing the cell line under conditions and time sufficient to express the viral proteins, which then form the particles. Thereafter, the particles can be purified by known techniques with care taken to insure that the structure of the particle is not destroyed. The particles can be used in a variety of areas. For example, they can be used to generate a desired immune reaction, to transform a cell with a heterologous nucleic acid sequence and/or to deliver a nucleic acid sequence to a desired host cell.

One can prepare transient or stable cell lines that express the lentiviral particles by standard techniques based upon the present teaching.

Thereafter, if stable cell lines are desired, one can screen for those cells that have been stably transfected by standard technique.

Such stable producer cell lines are a preferred source for obtaining packaged particles.

The particle of the present invention can be used to deliver heterologous DNA to a target cell. The target cell may be in vivo, in vitro or ex vivo. The target cell can be a dividing or preferably a quiescent cell. Quiescent cells include nonmitotic or postmitotic cells. The preferred nonmitotic cell is a macrophage. The target cells also include cells of the nervous system, e.g., neural or neuronal cells. Preferred quiescent or slowly dividing target cells include glia cells, myocytes, hepatocytes, pneumocytes, retinal cells, and hematopoietic stem cells. Pancreatic islet cell are also a preferred target.

Introduction of the viral particle carrying the heterologous gene to be delivered to a target cell may be effected by any method known to those of skill in the art. For example, with in vivo administration, the following techniquest are preferred. Catheters, injection, scarification, etc. For example, stereotaxic injection can be used to direct the viral particles to a desired location in the brain. Stereotaxic surgery is performed using standard neurosurgical procedures (Pellegrino and Cushman, (1971)). Additionally, the particles can be delivered by intracerebroventricular ("icv") infusion using a minipump infusion system, such as a SynchroMed Infusion System. A recent method based on bulk flow, termed convection, has also proven effective at delivering large molecules to extended areas of the brain and may be useful in delivering the viral particle to the target cell (Bobo et al., (1994); Morrison et al., (1994)). Other methods can be used including catheters, intravenous, parenteral, intraperitoneal and subcutaneous injection, oral or other known routes of administration.

In some instances one would use these vectors to transform host cells in vivo. One would inject a sufficient amount of the separate vectors or preferably the packaged viral particles to obtain a serum concentration in the tissue containing the target cell of the therapeutic protein ranging between about 1 pg/ml to 20 µg/ml. More preferably between about 0.1 µg/ml to 10 µg/ml. Still more preferably, between about 0.5 µg/ml to 10 µg/ml.

For example, solid dose forms that can be used for oral administration include capsules, tablets, pills, powders and granules. In such solid dose forms, the active ingredient, i.e., empty virus particle, is mixed with at least one inert carrier such as sucrose, lactose or starch. Such dose forms can also comprise additional substances other than inert diluents, e.g., lubricating agents, such as magnesium stearate. Furthermore, the does forms in the case of capsules, tablets and pills may also comprise buffering agents. The tablets, capsules and pills can also contain time-release coatings to release the particles over a predetermined time period.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the virus particle. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

The lentiviral vectors such as HIV-1 vectors can be produced by co-transfection of for instance vectors, pCMVgag-pol, pRev and pVSV-G cDNAs into 293T cells using Superfect (Olagen) [J. Richardson et al., *Gene Therapy*, 6:635–644 (1998)]. Cell culture supernatants are harvested 48–72 hours later. Ultracentrifugation are used to increase the titer of for example the VSV-G pseudotyped virions and result in obtaining titers of $10^6$ to $10^8$ infectious particles per ml. The vectors are normalized for reverse transcriptase activity. Transduction efficiencies can be measured on CD4+ SupT cells and 293T cells by FACS analysis of NGFR surface expression 48 hours after transduction.

Thereafter, the host cell can be transduced. For example, SupT cells are optimally transduced and selected for the marker, e.g. NGFR expression. Preferably at least $10^7$ transduced cells are isolated by known means, e.g. beads, affinity chromatography, etc. Cells are treated with the inducer, e.g., 1 µg/ml tetracycline, and allowed to go through two to four additional doublings so that more than one copy of each sFv intrabody gene is present in the pool of stably transduced cells. Approximately $5\times10^7$ to $1\times10^8$ cell in one to two ml are stained for identification of the desired phenotype, such as with the appropriate anti-CD4, CXCR4 or MHCI Mab followed by FITC-labeled antimouse IgG. The cells are sorted on for example, a MoFlo flow cytometer, which has high throughput capacity ($>5\times10^7$ cells/ml/hr). The lowest 10% of FITC labeled cells which will include dead cells, poorly stained cells and phenotypic knockout cells are collected and expanded in tissue culture. This procedure are repeated until populations of cells are recovered which are at least 50% negative for surface expression of the appropriate surface molecule.

A desired heterologous nucleic acid segment can be inserted into the empty lentiviral particle by a vector containing a nucleic acid segment of interest, the ori and a lentiviral packaging sequence necessary to package lentiviral RNA into the lentiviral particles. Preferably, the vector contains a 5' and 3' lentiviral LTR with the desired nucleic acid segment inserted between them. The nucleic acid segment preferably encodes a protein. One can create producer cell lines expressing virions and transform such cells with the packaging vector. The producer cell lines or any cell can be transformed by standard techniques. One preferred method is to use an inactivated adenovirus vector linked to the packaging vector by a condensing polycation such as polylysine or polyethylanimine (PEI) [see Baker, A. et al., *Nucleic Acids Res.*, 25(10):1950–1956 (1997); Baker, A. et al., *Gene Ther.*, 4(8):773–782 (1997); Scaria, A. et al., *Gene Ther.*, 2:295–298 (1995)]. The use of PEI is a polycation is preferred.

EXAMPLES

Construction of HIV-1 Mutant Plasmids

The E/E class 1 IN mutant was previously described (Jenkins et al., 1997). For the N/N mutant, the D64N change was incorporated into the Age I-PflM I (nucleotides 3,485–5,297) fragment in pNL43(D116N) using overlapping PCR (Engelman et al., 1995). Mutants pNL43 (E152Q) and pNL43(1-212) were similarly built by PCR. The pUC19 polylinker was modified to contain unique Age I and PflM I sites, and Age I-PflM I fragments containing N/N and E152Q were subcloned into modified pUC 19. A unique Xma I site was introduced at the cellular/LTR DNA boundary in the pNL4–3 5'-half genome plasmid p83–2 (Gibbs et al., 1994), generating p83–2/XmaI. The Aat II-Sph I fragment from p83–2/XmaI was swapped for the corresponding pNL4–3 fragment, generating pNL43/XmaI. For NNQ, the Bsm I-PflM I fragment containing E 152Q was swapped for the corresponding fragment in pUC19(N/N). The NNQ-containing Age I-PflM I fragment was then introduced back into pNL43/XmaI.

The U3U5 att mutant contained substitutions of TG for the conserved CAs at the ends of HIV-1. The U5 and U3 changes were first introduced into half-genome plasmids p83–2/XmaI and p83-10 (Gibbs et al., 1994) by PCR. Restriction fragments containing these changes were swapped for the corresponding fragments in pNL43/XmaI and pNL43/XmaI(NNQ), generating pNLX(U3U5) and pNLX(NNQ/LTR), respectively. The presence of each mutation, as well as the absence of off-site changes, was confirmed by sequencing PCR-generated DNAs.

Details for constructing the GFP-expression vector pHI.libGFP will be presented elsewhere (W. H. & J. S., in preparation). Briefly, the deleted gag/pol region was derived from v653 RtatpC (Parolin et al., 1996), and the env gene also contained a deletion. The gene for GFP was inserted as a BamH I-Not I cassette and was expressed as a multiply-spliced (nef–) message.

oriT was amplified from pMAMneo (Clontech) using Xho I and Not I-tagged primers. Plasmid pN/N.oriT came from ligating Xho I-digested oriT with Xho I-digested pNL43(N/N). Plasmid pGFP.oriT was constructed by ligating Not I-digested oriT with Not I-digested pHI.libGFP. For expressing TAg in cis from the HIV-1 LTR, NL4–3 nucleotides 8,785–9,017 in p83–10 were replaced with a Cla I-Not I-Xho I polylinker. Cla I-Not I-amplified TAg was inserted, followed by Not I-Xho I-tagged oriT. The Nhe I-Pml I fragment was then swapped for the corresponding fragment in pNLX(N/N), yielding pN/N.TAg-oriT. TAg was expressed as a subgenomic nef message. For CCR5-tropic derivatives, the EcoR I-BamH I fragment from pNL(AD8) (Englund et al., 1995) was swapped for the corresponding fragments in pNLX(N/N) and pN/N.TAg-oriT, yielding pN/N(AD8) and pN/N.TA-goriT(AD8), respectively.

Cells and Viruses

HeLa (American Type Tissue Collection CCL-2), 293T (Pear et al., 1993), COS-1 and CV1 cells were grown in Dulbecco modified Eagle medium containing 10% fetal calf serum (DMEM). T-cell lines were grown in RPMI 1640 containing 10% fetal calf serum (RPMI). Jurkat TAg cells were obtained from R. Bram, St. Jude Children's Research Hospital, Memphis, Tenn.

NL4–3 viruses were prepared by transfecting either HeLa or 293T cells in the presence of calcium phosphate (Sambrook et al., 1989). GFP viruses were prepared by cotransfecting 293T ($6 \times 10^5$ cells) in 6 well plates with 1.5 μg GFP vector, 1.5 μg CMV-P1-envpAvpu/vpr (Parolin et al., 1996) carrying either WT or D116A IN, 0.3 μg pHCMV-G (Yee et al., 1994), and 0.15 μg of rev-expression plasmid pSVCMV-rev. Transfected cell supernatants were tested for $Mg^{2+}$-dependent $^{32}$P-RT activity as described (Engelman et al., 1995).

Unless otherwise noted, T-cell lines ($2.0 \times 10^6$) were infected with $10^7$ $^{32}$P-RT cpm of WT or mutant HIV-1 in 0.5 ml for 90 min at 37° C., washed twice with serum-free RPMI, and resuspended in 5 ml of RPMI. Cultures were split at regular intervals and aliquots of the medium were assayed for $^{32}$P-RT activity. For DNA extractions, viruses were pretreated with DNase I (2 U/ml; Promega) at 37° C. for 30 min in the presence of 10 mM $MgCl_2$ to degrade residual plasmid DNA. CV-1 and COS-1 cells ($2 \times 10^5$) were infected with $3.4 \times 10^6$ RT-cpm of WT and mutant GFP viruses in 0.3 ml for 2 hr at 37° C. DMEM (2 ml) was added, cells were split at regular intervals, and aliquots were fixed and analyzed for GFP expression by fluorescence-activated cell sorting (FACS). Jurkat and Jurkat TAg cells ($2.0 \times 10^6$) were infected with $10^7$ RT-cpm of GFP viruses in 0.5 ml for 60 min at 37° C., washed once, and plated in 5 ml of RPMI. Cells were treated with TNF-α. (10 ng/ml) for 48 hr prior to fixing.

MDM were isolated essentially as previously described (Cayabyab et al., 1999). In brief, human PBMC ($5 \times 10^6$) isolated by Ficoll-Hypaque were incubated in 6-well plates for two days, recombinant human granulocyte macrophage colony stimulatory factor (1.0 μg/ml) and recombinant macrophage stimulatory factor (2.5 μg/ml) (PeproTech) were added for three days, nonadherent cells were removed by washing, and fresh medium containing cytokines was added. Four days later, cells were infected overnight with ~$10^7$ RT-cpm of HeLa-derived viruses, cells were washed, and fresh medium containing cytokines was added. About a third of this medium was replaced with fresh medium every third day.

The 1D Jurkat cell line was made by transfecting cells ($3 \times 10^6$) with 3 μg of pCMV-TAg (Campbell et al., 1997) using lipofectamine (Gibco BRL). G418 (0.8 mg/ml) was added after 2 days and cells were seeded into 96 well-plates ~2 weeks later. Individual G418-resistant colonies were expanded and assayed for TAg expression by Western blotting with monoclonal antibody PAb101 (Campbell et al., 1997). TAg-positive subclones were assayed for cell-surface CD4 expression by FACS.

Cell Fractionation, Southern Blotting and PCR

For cloning passed virus, cells were fractionated by the Hirt method as described (Freed and Martin, 1996). Supernatant DNA (4–10 μl) was amplified using Age I and PflM I-tagged primers and Pfu polymerase (Stratagene). The resulting fragments were either sequenced directly, or digested with Age I and PflM I and ligated to Age I-PflM I-digested pNL4–3. For Southern blotting and inverse PCR, cells ($3.0 \times 10^7$ MT-4; $4.0 \times 10^7$ 1D) were lysed in 1 ml of buffer K (20 mM HEPES, pH 7.5, 150 mM KCl, 5 mM $MgCl_2$, 0.025% digitonin, 1 mM DTT, 40 μg/ml aprotinin) and nuclei were recovered by centrifugation. Cytoplasmic DNA was recovered by precipitation with ethanol after RNase A treatment (0.1 mg/ml for 30 min at room temperature) and deproteinization. Nuclei were resuspended in 2 ml of buffer P1 (Qiagen) and lysed as recommended by the manufacturer. The supernatant after centrifugation was applied to an equilibrated Qiagen column and DNA was recovered as recommended by the manufacturer. The genomic DNA pellet was resuspended in 6 ml of buffer G (6M guanidine-HCl, 0.1 M sodium acetate, pH 5.5, 5% Tween 20, 0.5% Triton X-100) by heating at 56° C. for several hours. Dissolved DNA was recovered as described (Bowtell, 1987).

Southern blots were probed with a Xho I-Hind III riboprobe (HXB2 nucleotides 8,896–9,615). Levels of unintegrated DNA were quantified by phosphorimager (Molecular Dynamics). Integration was detected by inverse PCR essentially as previously described (Lewis et al., 1992). Genomic DNA (2–15 μg) digested with Hind III was recovered following extraction with phenol/chloroform and precipitation with ethanol. The DNA (500 ng) was ligated overnight in 50 μl at 16° C. with 1 U T4 DNA ligase (New England Biolabs). Following heat inactivation (65° C. for 10 min), DNA was recovered by precipitation with ethanol, resuspended in 10 μl $H_2O$ and 2 μl was amplified using nested PCR. The first round (50 μl) contained 0.5 μM each of AE459 (5'-GCTTTTTGCCTGTACTGGGTCTCTC) (SEQ ID NO: 1) and AE452 (5'-CACCATCCAAAGGTCAGTGGATATC) (SEQ ID NO:2) and 2 U of AmpliTaq DNA polymerase (Perkin Elmer) in buffer recommended by the manufacturer. Following heating at 95° C. for 2 min, the reactions were cycled 20 times by denaturing (95° C. for 15 sec), annealing (58° C. for 1 min), and extending (72° C. for 45 sec), followed by a 7 min extension at 72° C. DNA (2 μl) was transferred to a second PCR reaction (25 μl), and amplified as in the first round using 1 U of DNA polymerase, primers AE322 (5'-GGCTAACTAGGGAACCCACTG) (SEQ ID NO:3), AE 347 (5'-GTCAGTGGATATCTGATCCCTG) (SEQ ID NO:4) and 200,000 cpm of 5'-end labeled AE347. Reaction products were detected by autoradiography following polyacrylamide gel electrophoresis.

Cell-Type-Dependent HIV-1 IN and att Site Mutant Replication

To investigate the cell-type dependence of gene expression from unintegrated HIV-1 DNA, a variety of CD4-positive T-cell lines were infected with WT and mutant viruses. Two different class I IN mutants (N/N and E/E), one class II mutant (1–212), and one attachment (att) site mutant (U3U5) were initially analyzed. The N/N mutant contained substitutions of two (Asp64 and Asp 116 in HIV-1) of the three phylogenetically-conserved IN active site residues (reviewed in Brown, 1997). The E/E mutant contained substitutions of two lysine residues (156 and 159) important for IN-att DNA binding (Jenkins et al., 1997). The 1–212 class II mutant was a deletion lacking the C-terminal 76 amino acid residues of IN, and the U3U5 att site mutant contained base substitutions of the phylogenetically-conserved CA dinucleotides at the 3' termini of retroviral DNA (Brown, 1997).

Figure 1A:
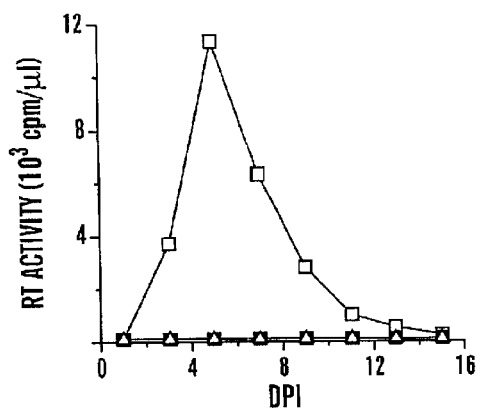
FIGS. 1A–1E show growth kinetics of WT and mutant HIV-1 in T-cell lines.
Figure 1B:
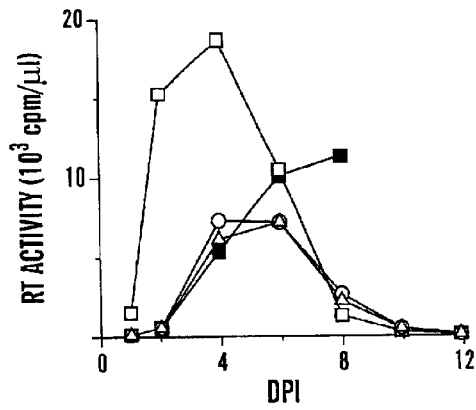

Preliminary experiments monitored cultures for HIV-1 replication after infecting $2 \times 10^6$ cells with $10^7$ $^{32}P$ RT-cpm (approximately $10^5$ infectious units of the NL4–3 strain; Vincenzi et al., 1994). Jurkat (Weiss et al., 1984) (FIG. 1a) and CEM-12D7 (Ross et al., 1991; data not shown) cells supported peak WT replication 5 and 7 days postinfection (Dpi), respectively. Neither of these cell lines supported detectable mutant virus replication over prolonged periods: Jurkat and CEM-12D7 cells infected with U3U5 were monitored for 1 month; Jurkat cells infected with IN mutants were monitored for 2 months (FIG. 1a and data not shown). C8166 T-cells (Salahuddin et al., 1983) supported peak WT replication 4 Dpi (FIG. 1b). Unexpectedly, C8166 cells also supported efficient replication of mutants N/N, E/E and U3U5 (FIG. 1b). Replication of IN mutant 1–212, however, was not detected under these conditions. MT-4 T-cells (Miyoshi et al., 1982) also supported replication of mutants N/N and E/E, but not 1–212 (FIG. 1c; U3U5 was not tested in MT-4). Thus, MT-4 and C8166 cells supported efficient replication of class I HIV-1 IN mutants, but not the class II 1–212 mutant (1–212 did not grow in MT-4 cells infected with $3.0 \times 10^7$ RT-cpm during 1 month of observation). Jurkat and CEM-12D7 cells, however, were additionally nonpermissive for replication of class I IN and att site mutants. Diluting virus 10–100-fold prior to infecting MT-4 cells delayed mutant N/N replication 1–2 weeks as compared to WT (data not shown).

Figure 1C:
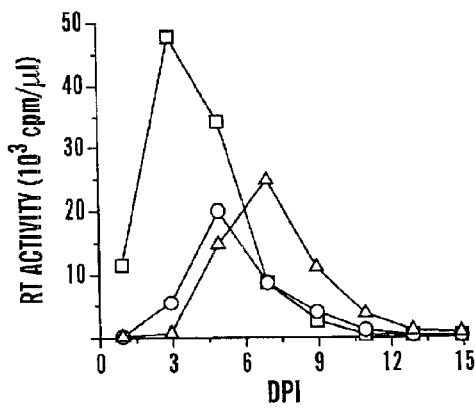
Figure 1D:
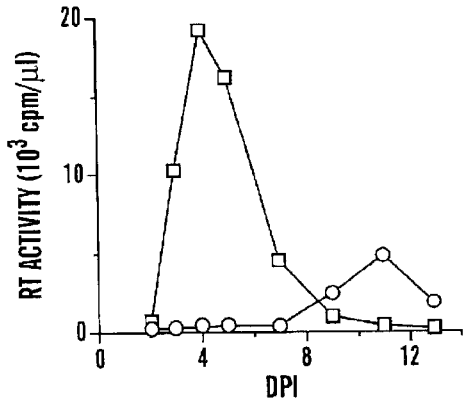

Since both C8166 and MT-4 were originally transformed with human T-cell leukemia virus type 1 (HTLV-1), we considered the possibility that pre-existing HTLV-1 IN might complement the HIV-1 defects in these infected cells. This seemed unlikely, since the U3U5 mutant was altered in the part of the att site that is conserved among all retroviruses, and grew as well as the class I IN mutants (FIG. 1b). However, to address this further, other HTLV-negative T-cell lines were screened for their ability to support class I IN mutant replication. Whereas neither H9 (Popvic et al., 1984) nor Molt-4 clone 8 (Kikukawa et al., 1986) cells supported detectable mutant replication (data not shown), N/N replicated in CEMx174 (Salter et al., 1985) cells (FIG. 1d).

Efficient Replication in the Absence of IN-Mediated Recombination

Figure 1E:
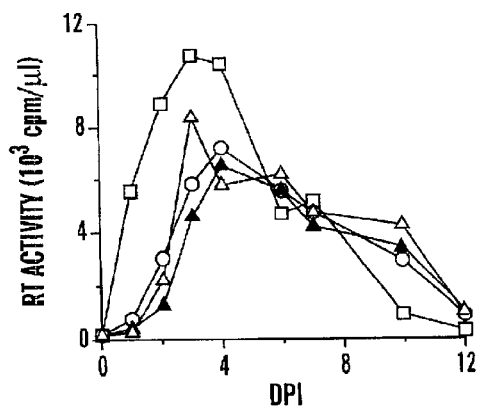

Viruses containing additional mutations were next analyzed for their abilities to replicate in permissive MT-4 cells. Glutamine was substituted for the remaining intact IN active site residue (Glu152) in N/N, yielding NNQ. NNQ was then combined with U3U5, yielding NNQ/LTR; NNQ/LTR differs from WT by seven nucleotide changes. The replication profiles of NNQ and NNQ/LTR in MT-4 cells were virtually identical to that of N/N (FIG. 1e), further indicating that HIV-1 can grow in a subset of T-cell lines in the absence of IN-mediated recombination.

To characterize class I IN mutant replication further, the supernatant from infected MT-4 cells (9 Dpi with $10^6$ RT-cpm of mutant N/N) was passed onto fresh MT-4 and Jurkat cells. Whereas Jurkat cells infected with $10^7$ RT-cpm of this virus did not support detectable replication, MT-4 cells infected with either $10^6$ or $10^7$ RT-cpm supported efficient HIV-1 replication (data not shown). MT-4 cells undergoing the second round of infection were lysed by Hirt extraction (Hirt, 1967), and HIV-1 in the cell supernatant was molecularly cloned and sequenced. All of the clones analyzed (6 total) retained both amino acid substitutions in the active site of the IN enzyme. Two of these clones were sequenced across their entire IN regions, and each sequence was identical to the starting N/N mutant (one clone had an A□G transition that did not alter the amino acid sequence). Thus, both the genotype and cell-type dependent replication phenotype of the class I IN mutant were maintained following two rounds of HIV-1 replication.

To address the mechanism of IN mutant replication further, WT and N/N-infected cells were fractionated and analyzed for HIV-1 DNA content. Unintegrated DNA was detected by Southern blotting, and integration was detected by inverse PCR (Lewis et al., 1992). The level of unintegrated WT DNA peaked in parallel with HIV-1 production, at 2 Dpi (FIGS. 2a and 2b). Replication was initially detected in N/N-infected cells 2 Dpi, and HIV-1 production increased over time roughly in parallel with the level of unintegrated DNA (FIGS. 2a and 2b). At the peak of replication (7 Dpi for N/N, 2 Dpi for WT), N/N-infected cells contained approximately 70% of the level of unintegrated HIV-1 DNA (FIGS. 2a and 2b) and produced about half as much virus as WT-infected cells (FIG. 1c). Significantly, the normal pattern of proviral integration was not detected in N/N-infected cells by inverse PCR (FIG. 2c, compare lanes 5–8 to lanes 3 and 4). A low level of integration was detected upon longer autoradiographic exposure; this level is consistent with the approximate $10^{-4}$ frequency of illegitimate recombination previously reported for class I IN mutant viruses (Leavitt et al., 1996; Gaur and Leavitt, 1998).

SV40-Dependent Episomal HIV-1 Replication

Although class I IN and att site mutants replicated in some cells, these integration-incompetent viruses did not grow in other cell lines. Since unintegrated DNA most likely contributed to IN mutant replication in permissive cells, we next tested if enhancing the replication of unintegrated HIV-1 DNA might override the block in nonpermissive cells. Many DNA viruses use viral proteins to promote episomal DNA replication from specific viral origins. Some of these, for example SV40, amplify their DNA copy number during replication (Cole, 1996). To initially test if elements of SV40 DNA replication would effect IN mutant replication in nonpermissive cells, the SV40 large tumor antigen (TAg) protein was stably introduced into Jurkat cells by transfection, and the SV40 origin of DNA replication (oriT) was cloned into the N/N mutant virus.

The replication of WT, N/N and N/N.oriT was assayed in Jurkat and its TAg-expressing 1D subclone. Whereas Jurkat cells infected with $10^7$ RT-cpm supported peak WT replication 7 Dpi, cells infected with either N/N or N/N.oriT did not yield detectable virus growth (data not shown). Infecting 1D cells with $10^7$ RT-cpm yielded peak WT replication 9 Dpi, but did not yield any detectable N/N replication (FIG. 3). Thus, the 1D cell line, like its Jurkat parent, was nonpermissive for class I IN mutant replication. In contrast, 1D cells infected with N/N.oriT supported a wild-type level of HIV-1 replication (FIG. 3). Diluting N/N.oriT as much as 1000-fold prior to infection did not alter its wild-type replication profile in 1D cells (FIG. 3 and data not shown). N/N.oriT grew like WT regardless if it was produced by transfection in 293T cells, which express the TAg protein, or HeLa cells, which do not express TAg (data not shown).

To test if the virus from N/N.oriT-infected 1D cells could initiate a spreading infection, it was passed onto fresh 1D and Jurkat cells. Whereas Jurkat cells infected with $10^6$ RT-cpm of this virus did not support detectable growth, 1D cells infected with either $10^6$ or $10^5$ RT-cpm supported efficient HIV-1 replication (data not shown). Thus, growing N/N.oriT in 1D cells yielded infectious HIV-1 that maintained its cell-type replication dependence upon passage. Passaged virus recovered from 1D cells was molecularly cloned and sequenced, and 6 of 6 clones retained both IN amino acid substitutions. Thus, N/N.oriT replication in 1D cells did not appear to rely on reversion to an integration-competent virus.

To address the mechanism of N/N.oriT replication further, WT, N/N and N/N.oriT-infected 1D cells were fractionated and analyzed for HIV-1 DNA content by Southern blotting and inverse PCR. Both WT and N/N.oriT replication peaked 3 Dpi in this experiment. As expected, inverse PCR detected a population of integrated proviruses in WT-infected genomic DNA (FIG. 4b, lane 3). Whereas about 40% of unintegrated N/N DNA was lost from the nonpermissive cells by 3 Dpi, the level of unintegrated N/N.oriT DNA increased approximately 10-fold as compared to the WT level (FIG. 4a). Significantly, genomic DNA from N/N.oriT-infected cells did not show signs of proviral integration by Southern blotting (data not shown) or inverse PCR (FIG. 4b, lane 4). Thus, IN-mediated recombination was not required for efficient HIV-1 replication under these conditions.

Transient Gene Expression from Episomal HIV-1 DNA

The results of the previous experiments showed that N/N.oriT replicated in a nonpermissive T-cell line if the TAg protein was present. Although efficient UV-1 replication occurred in the absence of detectable IN-mediated recombination, we investigated to what extent episomal versus illegitimately-integrated HIV-1 may have contributed to viral gene expression. For this, single-round infections were monitored for expression of green fluorescent protein (GFP) (Chalfie et al., 1994) from HIV-1-based vectors. Whereas cells harboring integrated vectors were expected to maintain relatively constant levels of GFP over time, cells infected with episomal vectors were predicted to display transient patterns of gene expression.

HIV-1 particles containing either WT IN or the class I mutant D116A (Ansari-Lari et al., 1995; Wiskerchen and Muesing, 1995) were pseudotyped with the vesicular stomatitis virus G (VSV-G) glycoprotein (Yee et al., 1994). The GFP expression profiles of three viruses, WT.GFP, D116A.GFP, and D116A.GFP.oriT, were monitored in two sets of cell lines; one member of each set expressed TAg protein, and the other member did not. COS-1 (Gluzman, 1981) is a TAg-expressing derivative of CV-1 (Jensen et al., 1964), and Jurkat TAg is a TAg-positive derivative of Jurkat (Jurkat TAg were subsequently determined to be CD4-negative; the following experiments were conducted prior to deriving 1D Jurkat).

Approximately 20% of CV-1 cells infected with WT.GFP were GFP-positive 3 Dpi (FIG. 5a). As expected, this level of expression was stable over an 11 day observation period. About 5% of CV-1 cells infected with D116A.GFP expressed GFP 3 Dpi. Significantly, this level of expression declined to background levels over the subsequent 8 days. Thus, extrachromosomal viral DNA supported transient HIV-1 gene expression in D116A.GFP-infected CV-1 cells. CV-1 cells infected with D116A.GFP.oriT behaved similarly to cells infected with D116A.GFP (FIG. 5a).

Almost 60% of COS-1 cells infected with WT.GFP were positive 3 Dpi, and this level remained fairly constant for the subsequent 13 days (FIG. 5b). The pattern of GFP expression from D 116A.GFP in COS-1 cells was similar to the pattern in CV-1; approximately 7% of the cells expressed GFP 3 Dpi, and this level declined to near background levels over the subsequent 13 days. In contrast to CV-1, about 50% of COS-1 cells infected with D116A.GFP.oriT were positive 3 Dpi (FIG. 5b). Significantly, this high level of GFP expression plummeted over the subsequent 13 days. Thus, episomal HIV-1 apparently supported the majority of GFP expression in D116A.GFP.oriT-infected COS-1 cells.

About 30% of Jurkat and Jurkat TAg cells infected with WT.GFP were GFP-positive 5–6 Dpi (FIGS. 5c and 5d). Unlike CV-1 and COS-1, GFP expression from D116A.GFP was undetectable in Jurkat cells (FIG. 5c) and barely detected over background in Jurkat TAg (FIG. 5d). This result is consistent with the observation that the N/N class I IN mutant did not detectably replicate in Jurkat (FIG. 1a). D116A.GFP.oriT also did not support detectable expression in Jurkat, but about 10% of Jurkat TAg were GFP-positive 3–5 Dpi. Similarly to COS-1, this level of GFP expression fell-off over the subsequent 11–13 days (FIG. 5d).

The Jurkat TAg cultures were monitored for an extended period of time. Whereas GFP expression was undetectable in D116A.GFP.oriT-infected cells after 16 Dpi, about 5% of WT.GFP-infected cells remained positive 51 Dpi. At this point, the cultures were treated with tumor necrosis factor α (TNF-α), an agent which can activate HIV-1 transcription in latently-infected cells (Duh et al., 1989). TNF-α increased the fraction of day 51 WT.GFP-infected positive cells from 5% to about 22%. Significantly, GFP expression in day 51 D116A.GFP.oriT-infected cells remained undetectable following TNF-α treatment (data not shown). We therefore conclude that extrachromosomal HIV-1 DNA supported the vast majority of GFP expression in D116A.GFP.oriT-infected COS-1 and Jurkat TAg cells.

Providing TAg in cis from the HIV-1 LTR Enables Class I IN Mutant Replication in Nonpermissive T-Cells and MDM The gene for TAg protein was next incorporated into the N/N.oriT virus itself to test if expressing TAg in cis from the HIV-1 LTR could drive non-integrating replication in nonpermissive cells. This significantly increased the size of the HIV-1 genome; whereas WT mRNA is approximately 9.1 kb, N/N.TAg-oriT is about 11.3 kb. N/N.oriT carrying the U19 mutant TAg protein defective for SV40 DNA replication (Jat et al., 1986) was built as a negative control.

Nonpermissive Jurkat cells were infected with $10^6$ RT cpm of WT, N/N.TAg-oriT, and N/N.U 19-oriT. Whereas WT replication peaked 8 Dpi, N/N.TAg-oriT growth peaked 12 Dpi (FIG. 6a). In repeated experiments, Jurkat infected with the TAg-oriT IN mutant yielded approximately 25% the level of virus released from WT-infected cells. Significantly, N/N.U19-oriT did not replicate (FIG. 6a), showing that N/N.TAg-oriT growth was dependent on a replication-competent TAg protein.

WT and N/N.TAg-oriT viruses derived from infected Jurkat cells were passed onto fresh Jurkat at two different multiplicities ($10^6$ and $10^5$ RT-cpm). The replication profiles of viruses passed at $10^6$ RT cpm were similar to their first round profiles (compare FIGS. 6b to 6a). Diluting viruses 10-fold prior to infection did not significantly delay the replication of N/N.TAg-oriT as compared to WT (compare FIG. 6c to FIG. 6b). At 16 Dpi, cells infected with first (FIG. 6a) and second (FIG. 6c) round N/N.TAg-oriT were lysed by Hirt extraction, and cell supernatants were analyzed by PCR using IN, TAg and oriT primers. Both TAg and oriT were maintained following virus passage (FIGS. 7a and 7b). Interestingly, an internal deletion in oriT arose during passage (FIG. 7b). The sequence of the IN PCR fragment from the second round lysate (FIG. 7a, lanes 2 and 3) was compared to the sequence of an amplified N/N plasmid control (lane 1). Significantly, this showed that both mutations in the IN active site were maintained following two rounds of N/N.TAg-oriT replication in Jurkat cells. Thus, a nonintegrating TAg-oriT HIV-1 strain stably replicated in nonpermissive Jurkat cells.

The replication capacities of WT, N/N, and N/N.TAg-oriT were next tested in primary MDM. For this, a set of CCR5-tropic viruses carrying the AD8 envelope glycoprotein (Englund et al., 1995) was constructed. MDM infected with WT(AD8) supported peak HIV-1 replication 10 Dpi. Consistent with previous reports (Englund et al., 1995; Wiskerchen and Muesing, 1995), the class I IN mutant N/N(AD8) did not detectably replicate (FIG. 8). Significantly, adding TAg-oriT to this defective virus drove HIV-1 replication in MDM. N/N.TAg-oriT(AD8) growth peaked the same day as WT, indicating this was due to a spreading HIV-1 infection (FIG. 8). In repeated experiments, MDM infected with N/N.TAg-oriT(AD8) yielded approximately 10% as much HIV-1 as WT(AD8)-infected cells.

Retroviral IN is incorporated into virions as the carboxyl terminal domain of large Pol-containing polyprotein precursors. Changes in IN exert pleiotropic effects on the viral life cycle. This has been most thoroughly studied for human immunodeficiency virus type 1 (HIV-1). Whereas some HIV-1 IN mutants (class I) are blocked specifically at the integration step, others (class II) display virus assembly and/or reverse transcription defects (Ansari-Lari et al., 1995; Engelman et al., 1995; Masuda et al., 1995; Wiskerchen and Muesing, 1995; Bukovsky and Göttlinger, 1996; Leavitt et al., 1996; for review, see Engelman, 1999). Cells infected with class I IN mutants contain more unintegrated circular DNA than cells infected with wild type (WT) HIV-1 (Engelman et al., 1995; Wiskerchen and Muesing, 1995; Leavitt et al., 1996). Class I mutants also display 10–20% of WT activity in the multinuclear activation of galactosidase indicator (MAGI) assay (Ansari-Lari et al., 1995; Engelman et al., 1995; Wiskerchen and Muesing, 1995), a single-round assay that requires de novo synthesis of the viral Tat protein in infected HeLa-derived target cells (Lewis et al., 1992; Kimpton and Emerman, 1992). Thus, although unintegrated HIV-1 DNA has not been shown to sustain a spreading viral infection, it can support some transient gene expression. In another single-round assay, however, RD cells infected with class I IN mutants carrying the gene for firefly luciferase did not display detectable luciferase activity (Masuda et al., 1995). Thus, the level of gene expression from unintegrated HIV-1 DNA apparently depends in part on the type of cell infected (Cara et al., 1995).

We have re-examined the growth characteristics of HIV-1 IN and att site mutants in a variety of cell types and find that a subset of transformed T-cell lines support efficient spreading infections of class I IN and att site mutants in the absence of normal provirus formation. In contrast, class II IN mutants did not grow in cell lines permissive for class I mutant replication. In addition, we find that extrachromosomal HIV-1 replication can be driven in both a nonpermissive T-cell line and primary monocyte-derived macrophages (MDM) by incorporating elements of simian virus 40 (SV40) episomal DNA replication.

Retroviral reverse transcription and integration take place in the context of a large nucleoprotein preintegration complex that is derived from the core of the infecting virion. Whereas perhaps 50% of completed reverse transcripts are competent for integration, a smaller number, which may not be suited for IN-mediated DNA recombination, is cyclized by host cell enzyme activities (Brown, 1997). Protein factors important for retroviral integration bind tightly to the LTR regions within preintegration complexes (Wei et al., 1997). Thus, these nucleoprotein complexes are probably inefficient templates for viral gene expression. Host mediated DNA circles, perhaps better transcriptional templates, probably do not possess mechanisms to replicate and segregate themselves to both daughters upon cell division. Unintegrated DNA circles have previously been shown to support at best transient HIV-1 gene expression (Cara et al., 1995; Engelman et al., 1995; Masuda et al., 1995; Wiskerchen and Muesing, 1995). Thus, the dogma was that efficient retroviral replication required a sustained level of gene expression that could only be supplied by an integrated provirus.

While IN-mediated integration of HIV-1 cDNA into infected cell chromatin is not absolutely required for virus replication, the amount of replication in the absence of the ORI varied considerably on a cell by cell basis. In a subset of T-cell lines, we found that host-mediated unintegrated DNA circles supported efficient spreading HIV-1 infections. In contrast, other T-cell lines, as well as primary MDM, were unable to sustain HIV-1 replication from unintegrated DNA templates. The replication blocks in these restrictive cell types, however, were overcome by incorporating a viral replicon such as cis- and trans-acting components of SV40 DNA replication, to the IN mutant genome.

While not wishing to be bound by theory, there likely exists a threshold level of gene expression within infected cells that supports the propagation of mutant viruses throughout the cultures, we believe that this level may be reached in some permissive cell lines because of a favorable transcriptional environment (Ross et al., 1991). In nonpermissive cell types, increasing the copy number of unintegrated DNA templates probably allows the requisite number of viral transcripts to be generated. Another parameter that may play a role in determining cell line permissivity is the stability of unintegrated DNA circles in V-1-infected cells. Quantifying levels of gene expression and half lives of unintegrated DNA in the different cell types may shed light on what contributes most to cell line permissivity. The rate and efficiency of virus entry may also play an important role in this determination (Srivastava et al., 1991).

Our results do make an important distinction between the requirements for HIV-1 integration versus the IN polypeptide. Cara et al. (1995) previously reported MDM-specific self-limiting replication of an HIV-1 IN deletion mutant. Without the addition of TAg and oriT, however, we were unable to detect any class I IN mutant growth in infected MDM (FIG. 8). Differences in HIV-1 strains and/or tissue culture conditions may account for these different results.

Retroviruses are widely used as vectors for human gene therapy. Although attractive for their ability to stably integrate into host cell chromosomes, this characteristic comes with a price as insertional mutagenesis is a safety concern for retroviral vectors (Shiramizu et al., 1994; Verma and Somia, 1997). One approach around this caveat is to fuse a specific DNA binding domain to IN to direct integration into specific DNA sequences in infected target cells (reviewed in Bushman, 1995). Although this works somewhat in in vitro integration assays, the ability to target retroviral integration in vivo has met with limited success (Katz et al., 1996; Bushman and Miller, 1997).

Nonintegrating episomal viral vectors also have wide applications in human gene therapy. For most of these vectors, the strategy is to supply transient high level gene expression in the absence of integration. SV40-based episomal vectors are currently introduced into cells ex vivo by transfection (Cooper et al., 1997). The results reported here suggest that SV40-based gene therapy vectors can be introduced into cells through retroviral-mediated infection. Future experiments will also test if bypassing the requirement for IN-mediated DNA recombination might improve the safety of live attenuated retroviral vaccines.

REFERENCES

1. Ansari-Lari, M. L., Donehower, L. A. and Gibbs, R. A. *Virology*, 211, 332–335 (1995).
2. Bowtell, D. D. L. *Anal. Biochem.*, 162, 463–465 (1987).
3. Brown, P. O. Integration. In Coffin, J. M., Hughes, S. H. and Varmus, H. E. (eds.), *Retroviruses*. Cold Spring Harbor, N.Y., pp. 161–203 (1997).
4. Bukovsky, A. and Göttlinger, H. *J. Virol.*, 70, 6820–6825 (1996).
5. Bushman, F. *Science*, 267, 1443–1444 (1995).
6. Bushman, F. D. and Miller, M. D. *J. Virol.*, 71, 458–464 (1997).
7. Campbell, K. S., Mullane, K. P., Aksoy, I. A., Stubdal, H., Zalvide, J., Pipas, J. M., Silver, P. A., Roberts, T. M., Schaffhausen, B. S. and DeCaprio, J. A. *Genes & Dev.*, 11, 1098–1110 (1997).
8. Cara, A., Guarnaccia, F., Reitz, M. S. Jr, Gallo, R. C. and Lori, F. *Virology*, 208, 242–248 (1995).
9. Cayabyab, M., Karlsson, G. B., Etemad-Moghadam, B. A., Hofmann, W., Steenbeke, T., Matilda, H., Fanton, J. W., Axthelm, M. K., Letvin, N. L. and Sodroski, J. G. *J. Virol.*, 73, 976–984 (1999).
10. Chalfie, M., Tu, Y., Euskirchen, G., Ward, W. W. and Prasher, D. C. *Science*, 263, 802–805 (1994).
11. Cole, C.N. *Fields Virology.* Lippincott-Raven, Philadelphia, pp. 1997–2025 (1996).
12. Cooper, M. J., Lippa, M., Payne, J. M., Hatzivassiliou, G., Reifenberg, E., Fayazi, B., Perales, J. C., Morrison, L. J., Templeton, D., Piekarz, R. L. and Tan, J. *Proc. Natl. Acad. Sci. USA*, 94, 6450–6455 (1997).
13. Duh, E. J., Maury, W. J., Folks, T. M., Fauci, A. S. and Rabson, A. B. *Proc. Natl. Acad. Sci. USA*, 86, 5974–5978 (1989).
14. Engelman, A., Englund, G., Orenstein, J. M., Martin, M. A. and Craigie, R. *J. Virol.*, 69, 2729–2736 (1995).
15. Engelman, A. *Adv. Virus Res.* (1999) (in press).
16. Englund, G., Theodore, T. S., Freed, E., Engelman, A. and Martin, M. A. *J. Virol.*, 69, 3216–3219 (1995).
17. Freed, E. O. and Martin, M. A. *J. Virol.*, 70, 341–351 (1996).
18. Gaur, M. and Leavitt, A. D. *J. Virol.*, 72, 4678–4685 (1998).
19. Gibbs, J. S, Regier, D. A. and Desrosiers, R. C. *AIDS Res. Hum. Retroviruses*, 10, 343–350 (1994).
20. Gluzman, Y. *Cell*, 23, 175–182 (1981).
21. Hirt, B. *J. Mol. Biol.*, 26, 365–369 (1967).
22. Jat, P. S., Cepko, C. L., Mulligan, R. C. and Sharp, P. A. *Mol. Cell. Biol.*, 6, 1204–1217 (1986).
23. Jenkins, T. M., Esposito, D., Engelman, A. and Craigie, R. *EMBO J.*, 16, 6849–6859 (1997).
24. Jensen, F. C., Girarcli, A. J., Gilden, R. V. and Koprowski, H. *Proc. Natl. Acad. Sci. USA*, 52, 53–59 (1964).
25. Katz, R. A., Merkel, G. and Skalka, A. M. *Virology*, 217, 178–190 (1996).
26. Kikukawa, R., Koyanagi, Y., Harada, S., Kobayashi, N., Hatanaka, M. and Yamamoto, N. *J. Virol.*, 57,1159–1162 (1984).
27. Kimpton, J. and Emerman, M. *J. Virol.*, 66, 2232–2239 (1992).
28. Leavitt, A. D., Robles, G., Alesandro, N. and Varmus, H. E. *J. Virol.*, 70, 721–728 (1996).
29. Lewis, P., Hensel, M. and Emerman, M. *EMBO J.*, 11, 3053–3058 (1992).
30. Masuda, T., Planelles, V., Krogstad, P. and Chen, I. S. Y. *J. Virol.*, 69, 6687–6696 (1995).
31. Miyoshi, I., Taguchi, H., Kubonishi, I., Yoshimoto, S., Ohrauki, Y., Shiraishi, Y. and Akagi, T. *Jpn. J. Cancer Res.*, 28, 219–228 (1982).
32. Parolin, C., Taddeo, B., Palu, G. and Sodroski, *J. Virology*, 222, 415–422 (1996).
33. Pear, W. S., Nolan, G. P., Scott, M. L. and Baltimore, D. *Proc. Natl. Acad. Sci. USA*, 90, 8392–8396 (1993).
34. Popvic, M., Samagadharan, M. G., Read, E and Gallo, R. C. *Science*, 224, 497–500 (1984).
35. Ross, E. K., Buckler-White, A. J., Rabson, A., Englund, G. and Martin, M. A. *J. Virol.*, 65, 4350–4358 (1991).

36. Salahuddin, S. Z., Markham, P. D., Wong-Staal, F., Franchini, G., Kalyanaraman, V. S. and Gallo, R. C. *Virology*, 129, 51–64 (1983).
37. Salter, R. D., Howell, D. N. and Cresswell, P. *Immunogenetics*, 21, 235–246 (1985).
38. Sambrook, J., Fritsch, E. F. and Maniatis, T. Molecular cloning. Cold Spring Harbor, N.Y. (1989).
39. Shiramizu, B., Herndier, B. G. and McGrath, M. S. *Cancer Res.*, 54, 2069–2072 (1994).
40. Srivastava, K. K., Fernandez-Larsson, R., Zinkus, D. M. and Robinson, H. L. *J. Virol.*, 65, 3900–3902 (1991).
41. Telesnitsky, A. and Goff, S. P. Reverse transcriptase and the generation of retroviral DNA. In Coffin, J. M., Hughes, S. H. and Varmus, H. E. (eds.), *Retroviruses*. Cold Spring Harbor, N.Y., pp. 121–160 (1997).
42. Vincenzi, E., Dimitrov, D. S., Engelman, A., Mignone, T.-S., Purcell, D. F. J., Leonard, J., Englund, G. and Martin, M. A. *J. Virol.*, 68, 7879–7890 (1994).
43. Verma, I. M. and Somia, N. *Nature*, 389, 239–242 (1997).
44. Wei, S-Q., Mizuuclhi, K. and Craigie, R. *EMBO J.*, 16, 7511–7520 (1997).
45. Weiss, A., Wiskocil, R. L. and Stobo, J. D. *J. Immunol.*, 133, 123–128 (1984).
46. Wiskerchen, M. and Muesing, M. A. *J. Virol.*, 69, 376–386 (1995).
47. Yee, J.-K., Miyanohara, A., LaPorte, P., Bouic, K., Burns, J. C. and Friedmann, T. *Proc. Natl. Acad. Sci. USA*, 91, 9564–9568 (1994).

All the references described herein are incorporated by reference.

What is claimed:

1. At least three vectors wherein a first vector contains a lentiviral gag gene encoding a lentiviral gag protein, wherein the lentiviral gag gene is operably linked to a promoter and a polyadenylation sequence, (2) a second vector containing an env gene encoding a functional envelope protein, wherein the env gene is operably linked to a promoter and a polyadenylation sequence; and (3) a lentiviral pol gene encoding a lentiviral pol protein, and wherein said lentiviral pol gene has been modified so that it expresses integrase that has been modified so that said integrase is not capable of integration, on one of the first two vectors or on at least a third vector, wherein said lentiviral pol gene is operably linked to a promoter and a polyadenylation sequence;

wherein said vectors do not contain sufficient nucleotides to encode the lentiviral gag and pol and the envelope protein on a single vector; and wherein said vectors do not contain nucleotides of the lentiviral genome referred to as a packaging segment to effectively package lentiviral RNA; and wherein the lentiviral proteins and the envelope protein when expressed in combination form a lentivirus virion containing an envelope protein around a lentiviral capsid; and (4) a packaging vector containing a nucleic acid sequence encoding a heterologous nucleic acid, wherein the nucleic acid sequence is operably linked to a promoter and a lentiviral packaging sequence necessary to package the lentiviral RNA into the lentiviral virion and contains at least a viral DNA origin of replication as part of an episomal replicon, wherein said episomal replicon comprises a viral DNA origin of replication and a sequence encoding a protein that acts as a replication transactivator.

2. The vectors of claim 1, wherein the packaging vector contains a gene encoding a protein that acts as a replication transactivator.

3. The vectors of claim 1, wherein the DNA viral origin of replication is from SIMIAN VIRUS 40, Epstein-Barr virus or BK virus.

4. The vectors of claim 1, wherein the lentivirus is a human immunodeficiency virus (HIV).

5. The vectors of claim 1, wherein the lentiviral pol gene is on the same vector as the lentiviral gag gene.

6. The vectors of claim 2, wherein the replication transactivator contains a portion of large T-antigen, for Simian Virus 40, large T-antigen for BK virus and EBNA-1 that transactivates a viral DNA origin of replication.

7. The vectors of claim 2 wherein the replication transactivator does not contain a domain that binds a human tumor suppressor gene product.

8. The vectors of claim 1, 2, 3, 6 or 7 wherein the env gene is heterologous to the lentiviral genome.

9. The vectors of claim 1, 2, 3, 6 or 7, wherein the heterologous nucleic acid is operably linked to an inducible promoter.

10. The vectors of claim 1, 2, 3, 6 or 7, wherein the lentivirus is a primate lentivirus, a feline immunodeficiency virus (FIV), a visna virus, or an equine infectious anemia virus.

11. The vectors of claim 1, 2, 3, 6 or 7, wherein the heterologous nucleic acid is a antisense molecule, a ribosome, or encodes a suicide gene, an antibody, a receptor, a cytokine, or a growth hormone.

12. The vectors of claim 11, wherein the heterologous nucleic acid sequence is a suicide gene.

13. The vector of claim 11, wherein the ribozyme or antisense molecule is capable of transplicing.

14. A vector system comprising:

(a) a first vector containing a lentiviral gag gene encoding a lentiviral gag protein, wherein the lentiviral gag gene is operably linked to a promoter and a polyadenylation sequence, (b) a second vector containing an env gene encoding a functional envelope protein, wherein the env gene is operably linked to a promoter and a polyadenylation sequence;

(c) lentiviral pol gene encoding a lentiviral pol protein, wherein said pol protein is at least integrase, wherein said integrase has been modified so that it is not capable of integration, and said pol gene is on the first or second vectors or on at least a third vector, wherein said lentiviral pol gene is operably linked to a promoter and a polyadenylation sequence;

wherein said at least first, second and third vectors do not contain sufficient nucleotides to encode be lentiviral gag and pol and the envelope protein on a single vector; and wherein said vectors do not contain nucleotides of the lentiviral genome referred to as a packaging segment to effectively package lentiviral RNA and;

wherein the lentiviral proteins and the envelope protein when expressed in combination form a lentivirus virion containing an envelope protein around a lentiviral capsid; and (d) a packaging vector containing a nucleic acid sequence encoding a target molecule, where the nucleic acid sequence is operably linked to a promoter directing transcription of the nucleic acid sequence in a desired cell and a lentiviral packaging sequence necessary to package the nucleic acid sequence encoding the target molecule into the lentiviral virion, and wherein said packaging vector also contains a functional episomal replicon comprising DNA viral origin of replication and a sequence encoding a protein that acts as a replication transactivator.

15. The vector system of claim 14, wherein the target molecule is selected form the group consisting of antisense molecules, therapeutic proteins, suicide molecules, signal transduction enzymes and antibodies.

* * * * *